United States Patent
Ogamino et al.

(10) Patent No.: US 9,242,978 B2
(45) Date of Patent: Jan. 26, 2016

(54) PHENYLACETAMIDE COMPOUND AND PHARMACEUTICAL CONTAINING SAME

(71) Applicant: KOWA COMPANY, LTD., Aichi (JP)

(72) Inventors: Takahisa Ogamino, Tokyo (JP); Shin Tanikawa, Tokyo (JP); Yoshiharu Miyake, Tokyo (JP); Shinsuke Itoh, Tokyo (JP); Yoshikazu Sawada, Tokyo (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 14/427,865

(22) PCT Filed: Sep. 25, 2013

(86) PCT No.: PCT/JP2013/005657
§ 371 (c)(1),
(2) Date: Mar. 12, 2015

(87) PCT Pub. No.: WO2014/050084
PCT Pub. Date: Apr. 3, 2014

(65) Prior Publication Data
US 2015/0218151 A1      Aug. 6, 2015

(30) Foreign Application Priority Data

Sep. 26, 2012   (JP) ................................ 2012-211623

(51) Int. Cl.
| | | |
|---|---|---|
| *C07D 401/12* | (2006.01) | |
| *C07D 403/12* | (2006.01) | |
| *C07D 417/12* | (2006.01) | |
| *A61K 31/4155* | (2006.01) | |
| *A61K 31/427* | (2006.01) | |
| *A61K 31/4439* | (2006.01) | |
| *A61K 31/497* | (2006.01) | |
| *C07D 417/14* | (2006.01) | |

(52) U.S. Cl.
CPC .......... *C07D 417/14* (2013.01); *A61K 31/4155* (2013.01); *A61K 31/427* (2013.01); *A61K 31/4439* (2013.01); *A61K 31/497* (2013.01); *C07D 401/12* (2013.01); *C07D 403/12* (2013.01); *C07D 417/12* (2013.01)

(58) Field of Classification Search
None
See application file for complete search history.

(56) References Cited

FOREIGN PATENT DOCUMENTS

| WO | WO 2004/072031 | 8/2004 |
| WO | WO 2005/123132 | 12/2005 |
| WO | WO 2008/116107 | 9/2008 |

OTHER PUBLICATIONS

Agius, "Targeting Hepatic Glucokinase in Type 2 Diabetes, Weighing the Benefits and Risks," Diabetes, vol. 58. pp. 18-20, Jan. 2009.
Ahren et al. "Inhibition of Dipeptidyl Peptidase-4 Reduces Glycemia, Sustanins Insulin Levels, and Reduces Glucagon Levels in Type 2 Diabetes," The J. of Clinical Endocrinology & Metabolism, 89(5), pp. 2078-2084, May 2004.
Bebemitz et al., "Investigation of Functionally Liver Selective Glucokinase Activators for the Treatment of Type 2 Diabetes," J. Med. Chem., 52, pp. 6142-6152, 2009.
Bonadonna et al., "Piragliatin (RO4389620), a Novel Glucokinase Activator, Lowers Plasma Glucose Both in the Postabsorptive State and after a Glucose Challenge in Patients with Type 2 Diabetes Mellitus: A Mechanistic Study," J. Clin. Endocrinol Metab., 95(11), pp. 5028-5036, Nov. 2010.
Fyfe et al., "Glucokinase Activator PSN-GK1 Displays Enhanced Antihyperglycaemic and Insulinotropic Actions," Diabetologia, 50, pp. 1277-1287, 2007.
Glaser et al., "Familial Hyperinsulinism Caused by an Activating Glucokinas Mutation," The New England J. of Medicine, vol. 338, pp. 226-230, Jan. 22, 1998.

(Continued)

*Primary Examiner* — Zinna Northington Davis
(74) *Attorney, Agent, or Firm* — Kenneth H. Sonnenfeld; Margaret B. Brivanlou; King & Spalding LLP

(57) ABSTRACT

The present invention is to create a compound that selectively activates glucokinase in the liver, and in particular, to provide an agent for treating and preventing diabetes and impaired glucose tolerance, wherein the agent has a low hypoglycemia risk. A compound represented by the formula (1) as shown below, or a salt thereof, or a solvate of the compound or the salt:
wherein, in the following formula (1), ring A represents a thiazolyl group, a pyridyl group, a pyrazyl group, or a pyrazolyl group; L represents —(CO)—, —(CS)—, or —SO$_2$—; and R$^1$ represents a C$_{1-6}$ alkyl group, a hydroxy C$_{1-6}$ alkyl group, a C$_{1-6}$ alkoxy group, an amino group, a C$_{1-6}$ alkylamino group, a hydroxyamino group, an N—C$_{1-6}$ alkylcarbamoyl group, or a group represented by the formula (2) as shown below, wherein R$^3$ represents a C$_{1-6}$ alkyl group; and R$^2$ represents a hydrogen atom, a halogen atom, a C$_{1-6}$ alkyl group, a C$_{1-6}$ alkoxy group, or a carboxyl group. The formulas are shown below:

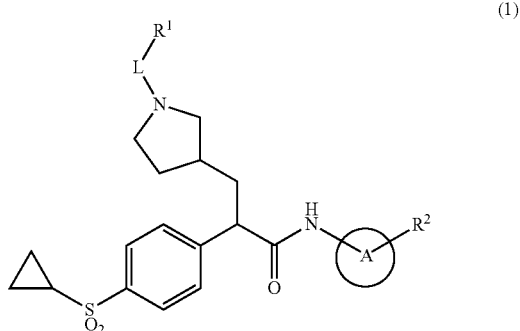

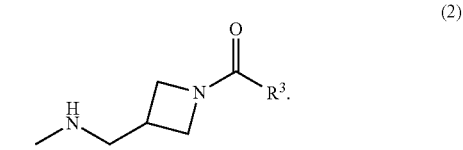

12 Claims, 1 Drawing Sheet

(56) References Cited

OTHER PUBLICATIONS

Matschinksy et al., "Glucokinase Activators for Diabetes Therapy," Diabetes Care, 34(2), pp. S236-S243, May 2011.
Nielsen et al., "Pharmacology of Exenatide (synthetic exendin-4): a Potential Therapeutic for Improved Glycemic Control of Type 2 Diabetes," Regulatory Peptides, 117, pp. 77-88, 2004.
Pfefferkorn et al., "Discovery of (S)-6-(3-Cyclopentyl-2(-4-(Trifluoromethyl)-1H-imidazol-1-yl)propanamido)nicotinic Acid as a Hepatoselective Glucokinase Activator Clinical Candidate for Treating Type 2 Diabetes Mellitus," J. of Medicinal Chemistry, J. Med. Chem., 55, pp. 1318-1333, 2012.
Sturgess, et al., "The Sulphonylurea Receptor May be an ATP-Sensitive Potassium Channel," The Lancet, pp. 474-475, Aug. 31, 1985.
Vionnet et al., "Nonsense Mutation in the Gluokinas Gene Causes Early-Onset Non-insulin-Dependent Diabetes Mellitus," Nature, 356, pp. 721-722, Apr. 23, 1992.

PHENYLACETAMIDE COMPOUND AND PHARMACEUTICAL CONTAINING SAME

TECHNICAL FIELD

The present invention relates to a novel compound having a glucokinase-activating action. In addition, the present invention also relates to a pharmaceutical composition for treating or preventing diabetes and the like, which comprises a glucokinase-activating compound as an active ingredient.

BACKGROUND ART

According to a Summary of National Health and Nutrition Examination Survey Results 2007 published by the Ministry of Health, Labour and Welfare, it is estimated that there are approximately 8,900,000 people who are "strongly suspected of having diabetes" and approximately 13,200,000 people who are "likely to have diabetes" in Japan. That is to say, it is predicted that a total of approximately 22,100,000 Japanese people are affected with diabetes or belong to a diabetes high-risk group. Diabetes has characteristics such as an increase in the fasting plasma glucose level, insulin resistance, acceleration of gluconeogenesis in the liver, and a reduction in glucose-responsive insulin secretion. In addition, there is a fear that diabetes may increase the risk of developing diabetic nephropathy, retinopathy, nervous disorder, and macroangiopathy, and that it may further lead to a significant reduction in quality of life (QOL), such as the necessity of dialysis, blindness, quadruple amputation, arteriosclerotic disease, and stroke.

For the treatment of diabetes, kinesitherapy, dietetic therapy, and drug therapy are carried out. As agents used in drug therapy, metformin having the action of suppressing gluconeogenesis in the liver and promoting the use of sugar in the skeletal muscle is used as a first-line drug. Then, a sulfonylurea (SU) agent promoting insulin secretion, a dipeptidyl peptidase (DPP)-4 inhibitor (see non-patent document 1), a glucagon-like peptide (GLP)-1 analog (see non-patent document 2), thiazolidinedione that improves insulin resistance, and the like are used as agents of second alternatives. Among these agents, the SU agent stimulates pancreatic β-cells and promotes endogenous insulin secretion (see non-patent document 3). However, there is a case in which the SU agent may cause hypoglycemia as a side effect. Thus, attention should be paid when this agent is used, in particular, for elder people, people with deterioration of renal function, and the case of an irregular dietary habit. In addition, with regard to the SU drug, side effects such as an increase in body weight have also been reported. Moreover, the SU drug has been known to cause primary failure in which no effects are found from an initial administration, or secondary failure in which clinical effects disappear during the administration period.

Glucokinase (hereinafter also abbreviated as "GK") belongs to a hexokinase family and has an alias "hexokinase IV." Hexokinase is an enzyme that catalyzes conversion of glucose to glucose-6-phosphate at an initial stage of the glycolysis system in a cell. In the case of three hexokinases other than GK, enzymatic activity becomes saturated at a glucose level of 1 mmol/L or less. On the other hand, GK has low affinity for glucose and shows a Km value close to a physiological blood glucose level (8 to 15 mmol/L). GK is mainly expressed in liver and pancreatic β-cells. In recent years, it has been elucidated that GK is also present in brain. The sequences of N-terminal 15 amino acids are different between GK in the liver and GK in pancreatic β-cells, depending on a difference in splicing. However, they have identical enzymatic properties, and intracellular glucose metabolism via GK is accelerated in response to a change in blood glucose levels from a normal blood glucose level (around 5 mM) to hyperglycemic level after eating (10 to 15 mmol/L).

Through the ages, a hypothesis had been proposed that GK functions as a glucose sensor in the liver and pancreatic β-cells. Recent study results have demonstrated that GK actually plays an important role for the maintenance of systemic glucose homeostasis, so that the hypothesis could be proved. For example, a mouse with a destroyed glucokinase gene had significant hyperglycemic symptoms and died shortly after birth. In addition, in heterozygous GK knockout mice, glucose tolerance was deteriorated and insulin secretion by sugar stimulation was impaired. On the other hand, in normal mice in which GK was excessively expressed, the lowering of a blood glucose level, an increase in the content of glycogen in liver tissues, and the like were observed, and such phenomena were observed also in mice in which diabetes was artificially developed. Furthermore, recent studies have revealed that GK functions as a glucose sensor and plays an important role for the maintenance of glucose homeostasis even in humans. An abnormality in the GK gene was found in a family line of maturity-onset diabetes of the young referred to as "MODY2," and the correlation between the symptoms of this disease and GK activity was clarified (non-patent document 4). Meanwhile, a family line having mutagenesis for increasing GK activity was also found. In such a family line, fasting hypoglycemic symptoms attended with an increase in the plasma insulin level were also observed (non-patent document 5). From these reports, it is considered that GK functions as a glucose sensor in mammals including humans and plays an important role for regulation of blood glucose. Accordingly, it is considered that a substance having a GK-activating action is useful as an agent for sugar metabolism-related diseases including type II diabetes as a typical example.

According to several reports regarding GK-activating drugs, it has been revealed that there is a considerable risk that drug administration will cause hypoglycemia (non-patent documents 6 and 7). Excessive induction of insulin secretion in the pancreas in a state in which the blood glucose level is low has been suggested as a major cause of the occurrence of this hypoglycemia. A GK-activating drug having a systemic action (pancreas and liver) is considered to have the hypoglycemia risk. Moreover, a GK-activating action in the pancreas is considered to increase stress in pancreatic β-cells, and thus, as in the case of the sulfonylurea agent, the GK-activating drug has the risk of causing dysfunction of the β-cells and deterioration of diabetes, when it is administered for a long period of time. Furthermore, this drug also has the risk of leading to an increase in the amount of body fat and an increase in body weight due to insulin secretion.

As means for avoiding these problems regarding side effects, several GK-activating drugs with high liver selectivity have been reported. For example, patent document 1 describes a thought that blood glucose level can be normalized, while reducing the hypoglycemia risk, by using a liver-selective GK-activating factor. This document describes that the urea compound described in WO2004/002481 was used for evaluation, but does not disclose the chemical structure of a specific compound. In addition, non-patent document 8 reports that a compound represented by the following formula (A):

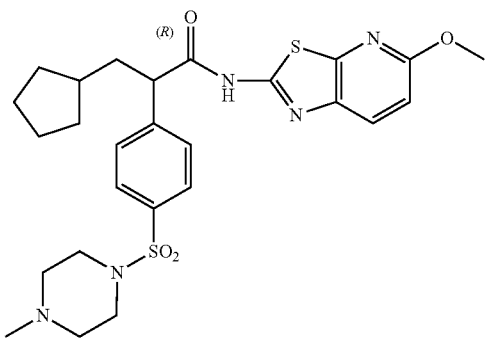

(A)

is a liver-selective GK-activating drug for lowering blood glucose level without increasing insulin secretion. However, this document reports that the aforementioned compound is distributed, rather in a larger amount, in the pancreas, and thus, the action mechanism of liver selectivity has not been clarified. Moreover, non-patent document 9 reports that a compound represented by the following formula (B):

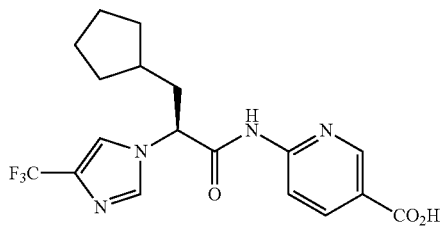

(B)

acts as a liver-selective GK-activating drug by being incorporated into the liver by organic anion transporters (OATP1B1 and OATP1B3), by utilizing carboxylic acid substitution on pyridine. However, this document also reports that if the substitution site of carboxylic acid is moved, the pharmacological activity itself disappears.

In the liver, GK is regulated by a glucokinase regulatory protein (GKRP). GKRP competing with glucose binds to GK and then inhibits it. At a physiological glucose level, a majority of GK in the liver binds to GKRP, and it is localized in the nucleus of a hepatocyte. In contrast, at a high glucose level, GK does not bind to GKRP, and thus, phosphorylation of glucose becomes possible. As such, by the action of GKRP, GK activity is regulated in a glucose-dependent manner in the liver (non-patent document 10). In fact, when a liver-selective GK-activating drug was repeatedly administered to Goto-Kakizaki diabetes model rats, the drug exhibited a hypoglycemic action at the same level as that of a systemic GK-activating drug. On the other hand, when such a liver-selective GK-activating drug was repeatedly administered to normal rats, the drug did not lower the blood glucose level, while a systemic GK-activating drug lowered the blood glucose level of the normal rats. As a result, it was demonstrated that the liver-selective GK-activating drug has the hypoglycemia risk that is lower than that of the systemic GK-activating drug (non-patent document 9). From these results, the liver-selective glucokinase-activating drug is anticipated to be a new type of glucokinase-activating antidiabetic drug, which reduces side effects caused by systemic GK-activating drugs by controlling blood glucose level in a glucose-dependent manner. However, as described above, there have been only a few reports regarding liver-selective GK-activating drugs, and thus, it is still difficult to design a liver-selective compound intentionally.

As an antidiabetic drug having the phenylacetamide skeleton of the present invention, which is based on a GK-activating action, a compound represented by the following formula (C) has been reported (patent document 2).

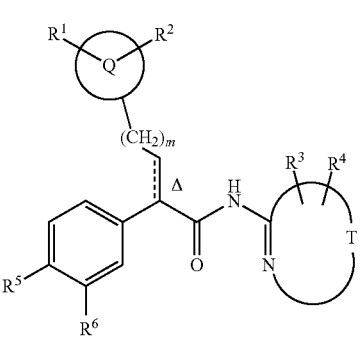

(C)

(wherein Q represents aryl, 5- or 6-membered ring heteroaryl, or 4- to 8-membered heterocycle; T represents a heterocycle, which is linked to form a heteroaryl ring together with —N═C—, or in which only the N═C bond is an unsaturated portion; $R^1$ and $R^2$ each independently represent hydrogen, hydroxy, halogen, cyano, nitro, vinyl, ethynyl, methoxy, $OCF_nH_{3-n}$, —N ($C_{0-4}$ alkyl)($C_{0-4}$ alkyl), CHO, or $C_{1-2}$ alkyl (which is optionally substituted with one to five independent substituents selected from halogen, hydroxy, cyano, methoxy, —N ($C_{0-2}$ alkyl) ($C_{0-2}$ alkyl), $SOCH_3$, and $SO_2CH_3$); or $R^1$ and $R^2$ together form a carbon ring or a heterocycle; or $R^1$ and $R^2$ may together represent an oxygen atom linked to a ring via a double bond; $R^3$ and $R^4$ each independently represent hydrogen, halogen, $OCF_nH_{3-n}$, methoxy, $CO_2R^{77}$, cyano, nitro, CHO, $CONR^{99}R^{100}$, $CON(OCH_3)CH_3$, or $C_{1-2}$ alkyl, heteroaryl or $C_{3-7}$ cycloalkyl, which is optionally substituted with one to five independent substituents selected from halogen, hydroxy, cyano, methoxy, —$NHCO_2CH_3$, and N($C_{0-2}$ alkyl) ($C_{0-2}$ alkyl); or $R^3$ and $R^4$ together form a 5- to 8-membered aromatic ring, a heteroaromatic ring, a carbon ring, or a heterocycle; $R^5$ and $R^6$ each independently represent hydrogen, hydroxy, halogen, cyano, nitro, $CO_2R^7$, CHO, $COR^8$, $C(OH)R^7R^8$, $C(═NOR^7)$ $R^8$, $CONR^9R^{10}$, $SR^7$, $SOR^8$, $SO_2R^8$, $SO_2NR^9R^{10}$, $CH_2NR^9R^{10}$, $NR^9R^{10}$, N($C_{0-4}$ alkyl) $SO_2R^8$, $NHCOR^7$, or a $C_{1-4}$ alkyl group, a $C_{2-4}$ alkenyl group, a $C_{2-4}$ alkynyl group, a $C_{1-4}$ alkoxy group, an aryl group or a heteroaryl group, in which any group is optionally substituted with one to six independent substituents selected from halogen, cyano, nitro, hydroxy, $C_{1-2}$ alkoxy, —N ($C_{0-2}$ alkyl) ($C_{0-2}$ alkyl), $C_{1-2}$ alkyl, $CF_nH_{3-n}$, aryl, heteroaryl, —$COC_{1-2}$ alkyl, —CON ($C_{0-2}$ alkyl)($C_{0-2}$ alkyl), $SCH_3$, $SOCH_3$, $SO_2CH_3$, and $SO_2N(C_{0-2}$ alkyl)($C_{0-2}$ alkyl); or $R^5$ and $R^6$ together form a 5- to 8-membered carbon ring or a heterocycle; $R^7$ and $R^{77}$ each independently represent hydrogen, or a $C_{1-4}$ alkyl group, a $C_{2-4}$ alkenyl group, a $C_{2-4}$ alkynyl group, a $C_{3-7}$ cycloalkyl group, an aryl group, a heteroaryl group or 4- to 7-membered heterocyclic group, in which any group is optionally substituted with one to six independent substituents selected from halogen, cyano, nitro, hydroxy, $C_{1-2}$ alkoxy, —N ($C_{0-2}$ alkyl) ($C_{0-2}$ alkyl), $C_{1-2}$ alkyl, $C_{3-7}$ cycloalkyl, a 4- to 7-membered heterocycle, $CF_nH_{3-n}$, aryl, heteroaryl, $CO_2H$, —$COC_{1-2}$ alkyl, —CON ($C_{0-2}$ alkyl)($C_{0-2}$ alkyl), $SOCH_3$, $SO_2CH_3$, and $SO_2N(C_{0-2}$ alkyl)($C_{0-2}$ alkyl); $R^8$ represents a $C_{1-4}$ alkyl group, a $C_{2-4}$ alkenyl group, a $C_{2-4}$ alkynyl group, a $C_{3-7}$ cycloalkyl group, an aryl group, a heteroaryl group, or a 4- to 7-membered heterocyclic group, in which any group is optionally substituted with one to six independent substituents selected from halogen, cyano, nitro, hydroxy, $C_{1-2}$ alkoxy, —N ($C_{0-2}$ alkyl)($C_{0-2}$ alkyl), $C_{1-2}$ alkyl, $C_{3-7}$ cycloalkyl, a 4- to 7-membered heterocycle, $CF_nH_{3-n}$, aryl, heteroaryl, $CO_2H$, $COC_{1-2}$ alkyl, —CON ($C_{0-2}$ alkyl) ($C_{0-2}$ alkyl), $SOCH_3$, $SO_2CH_3$, and $SO_2N(C_{0-2}$ alkyl) ($C_{0-2}$ alkyl); $R^9$, $R^{10}$, $R^{99}$, and $R^{100}$ each independently represent hydrogen, or a $C_{1-4}$ alkyl group, a $C_{3-7}$ cycloalkyl group, an aryl group, a heteroaryl group or a 4- to 7-membered heterocyclic group, in which any group is optionally substituted with one to six independent substituents selected from halogen, cyano, nitro, hydroxy, $C_{1-2}$ alkoxy, —N ($C_{0-2}$ alkyl) ($C_{0-2}$ alkyl), $C_{1-2}$ alkyl, $C_{3-7}$ cycloalkyl, a 4- to 7-membered heterocycle, $CF_nH_{3-n}$, aryl, heteroaryl, $COC_{1-2}$ alkyl, —CON ($C_{0-2}$ alkyl) ($C_{0-2}$ alkyl), $SOCH_3$, $SO_2CH_3$, and $SO_2N(C_{0-2}$ alkyl) ($C_{0-2}$ alkyl); or $R^9$ and $R^{10}$, or $R^{99}$ and $R^{100}$ together form a 6- to 8-membered hetero bicyclic system or a 4- to 8-membered heterocycle, which is optionally substituted with one or two independent substituents selected from $C_{1-2}$ alkyl, $CH_2OCH_3$, $COC_{0-2}$ alkyl, hydroxy, and $SO_2CH_3$; n represents 1, 2, or 3; m represents 0 or 1; and the dotted line optionally forms a double bond together with the solid line, and Δ indicates that the double bond is in (E)-configuration). However, the aforementioned compound is different from the compound of the invention of the present application in terms of the substituents $R^1$ and $R^2$ on the ring Q. Moreover, as for the aforementioned compound there are neither descriptions nor suggestions of possessing a liver-selective action. It has been reported that, in particular, the compound of Example 94 (PSN-GK1), which is a representative compound, has a hypoglycemic action on normal mice, even if it is used at a low dose (non-patent document 11).

PRIOR ART DOCUMENTS

Patent Documents

Patent Document 1: WO2005/123132
Patent Document 2: WO2004/072031

Non-Patent Documents

Non-patent Document 1: J. Clin. Endocrinol. Metab., 89(5), 2078-2084 (2004)
Non-patent Document 2: Regul. Pept., 117(2), 77-88 (2004)
Non-patent Document 3: The Lancet, 326(8453),474-475 (1985)
Non-patent Document 4: Nature, 356(6371), 721-2 (1992)
Non-patent Document 5: N. Engl. J. Med., 338(4), 226-30 (1998)
Non-patent Document 6: J. Clin. Endocrinol. Metab., 95(11), 5028-5036 (2010)
Non-patent Document 7: Diabetes care, 34(2) S236-S243 (2011).
Non-patent Document 8: J. Med. Chem., 52(19) 6142-6152 (2009)
Non-patent Document 9: J. Med. Chem., 55(3) 1318-1333 (2012).
Non-patent Document 10: Diabetes, 58(1) 18-20 (2009).

Non-patent Document 11: Diabetologia, 50 (6) 1277-1287 (2007).

SUMMARY OF THE INVENTION

Problem to be Solved by the Invention

The present invention is to create a compound that selectively activates glucokinase in the liver, and in particular, to provide an agent for treating and preventing diabetes and impaired glucose tolerance, wherein the agent has a low hypoglycemia risk.

Means to Solve the Problem

Under such circumstances, the present inventors have conducted intensive studies. As a result, the inventors have found that a compound represented by the formula (1) as shown below has the excellent glucokinase-activating action with a low hypoglycemia risk by acting on hepatic glucokinase selectively, and thus completed the present invention.

Specifically, the present invention relates to the following inventions.

[1] A compound represented by the following formula (1), or a salt thereof, or a solvate of the compound or the salt:

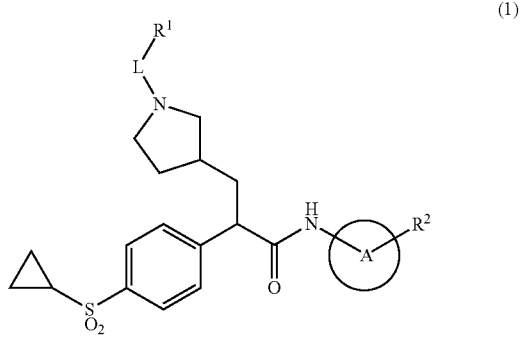

(1)

[wherein ring A represents a thiazolyl group, a pyridyl group, a pyrazyl group, or a pyrazolyl group,
L represents —(CO)—, —(CS)—, or —(SO$_2$)—,
$R^1$ represents a $C_{1-6}$ alkyl group, a hydroxy $C_{1-6}$ alkyl group, a $C_{1-6}$ alkoxy group, an amino group, a $C_{1-6}$ alkylamino group, a hydroxyamino group, an N—$C_{1-6}$ alkylcarbamoyl group, or a group represented by the following formula (2):

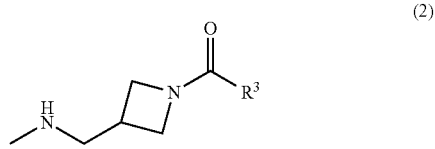

(2)

wherein $R^3$ represents a $C_{1-6}$ alkyl group, and $R^2$ represents a hydrogen atom, a halogen atom, a $C_{1-6}$ alkyl group, a $C_{1-6}$ alkoxy group, or a carboxyl group].

[2] A pharmaceutical composition comprising the compound or a salt thereof, or a solvate of the compound or the salt according to [1] above, and a pharmaceutically acceptable carrier.

[3] A glucokinase-activating agent comprising the compound, or a salt thereof, or a solvate of the compound or the salt according to [1] or [2] above, as an active ingredient.

[4] A hypoglycemic agent comprising the compound, or a salt thereof, or a solvate of the compound or the salt according to [1] or [2] above, as an active ingredient.

[5] An agent for preventing and/or treating at least one disease selected from the group consisting of diabetes, impaired glucose tolerance, gestational diabetes, a chronic complication of diabetes (including diabetic peripheral neuropathy, diabetic nephropathy, diabetic retinopathy, and diabetic arteriosclerosis), and metabolic syndrome, wherein the agent comprises the compound, or a salt thereof, or a solvate of the compound or the salt according to [1] or [2] above, as an active ingredient.

[6] A method for activating glucokinase, which comprises administering an effective amount of the compound or a salt thereof, or a solvate of the compound or the salt according to [1] or [2] above.

[7] A method for lowering blood glucose level, which comprises administering an effective amount of the compound, or a salt thereof, or a solvate of the compound or the salt according to [1] or [2] above.

[8] A method for preventing and/or treating at least one disease selected from the group consisting of diabetes, impaired glucose tolerance, gestational diabetes, a chronic complication of diabetes (including diabetic peripheral neuropathy, diabetic nephropathy, diabetic retinopathy, and diabetic arteriosclerosis), and metabolic syndrome, wherein the method comprises administering an effective amount of the compound, or a salt thereof, or a solvate of the compound or the salt according to [1] or [2] above.

[9] The compound, or a salt thereof, or a solvate of the compound or the salt according to [1] or [2] above, which is used for activation of glucokinase.

[10] The compound, or a salt thereof, or a solvate of the compound or the salt according to [1] or [2] above, which is used for lowering blood glucose level.

[11] The compound, or a salt thereof, or a solvate of the compound or the salt according to [1] or [2] above, which is used for preventing and/or treating at least one disease selected from the group consisting of diabetes, impaired glucose tolerance, gestational diabetes, a chronic complication of diabetes (including diabetic peripheral neuropathy, diabetic nephropathy, diabetic retinopathy, and diabetic arteriosclerosis), and metabolic syndrome.

[12] Use of the compound, or a salt thereof, or a solvate of the compound or the salt according to [1] or [2] above, for production of a glucokinase-activating agent.

[13] Use of the compound, or a salt thereof, or a solvate of the compound or the salt according to [1] or [2] above, for production of a hypoglycemic agent.

[14] Use of the compound, or a salt thereof, or a solvate of the compound or the salt according to [1] or [2] above, for production of an agent for preventing and/or treating at least one disease selected from the group consisting of diabetes, impaired glucose tolerance, gestational diabetes, a chronic complication of diabetes (including diabetic peripheral neuropathy, diabetic nephropathy, diabetic retinopathy, and diabetic arteriosclerosis), and metabolic syndrome.

Effect of the Invention

The phenylacetamide compound of the present invention has a liver-selective GK-activating action, and it is able to avoid side effects caused by activation of pancreatic GK (in particular, the hypoglycemia risk). Thus, the present phenylacetamide compound is useful as a pharmaceutical preparation for preventing and/or treating a disease selected from the group consisting of diabetes, impaired glucose tolerance, gestational diabetes, a chronic complication of diabetes (including diabetic peripheral neuropathy, diabetic nephropathy, diabetic retinopathy, and diabetic arteriosclerosis), and metabolic syndrome, in hematherms (which are preferably mammals including humans). Preferred diseases include diabetes and impaired glucose tolerance. The phenylacetamide compound of the present invention can be preferably used as a pharmaceutical preparation for treating the aforementioned diseases.

MODE OF CARRYING OUT THE INVENTION

Figure 1:
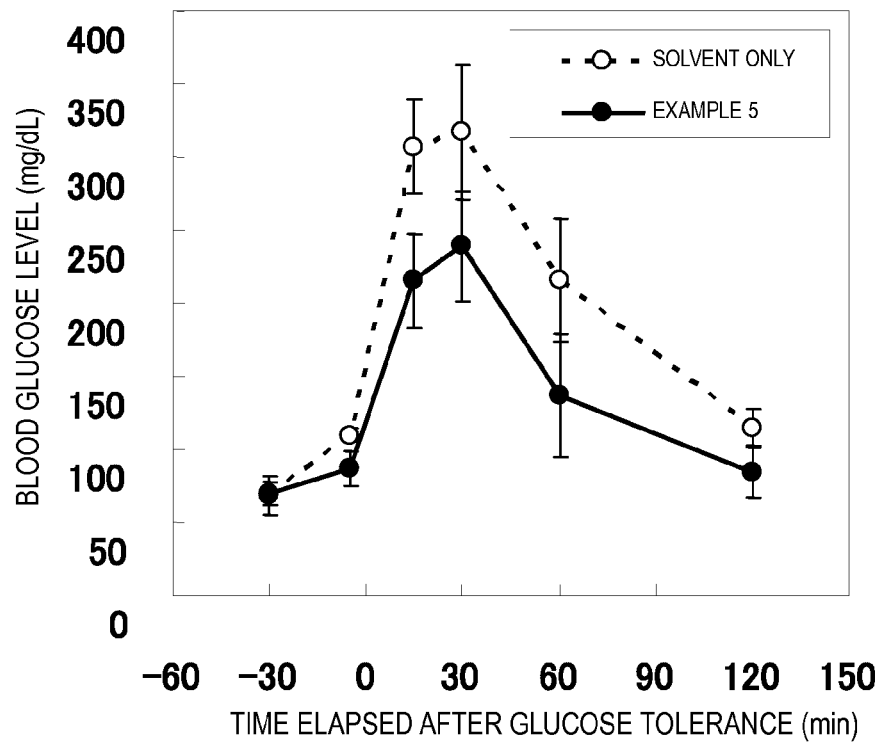
FIG. 1 is a view showing the results of an oral sugar tolerance test that was carried out after completion of a single administration of the compound of the present invention to normal mice.

In the present description, examples of the "halogen atom" include a fluorine atom, a chlorine atom, a bromine atom, and an iodine atom.

In the present description, the term "$C_{1-6}$ alkyl group" refers to a linear or branched alkyl group containing 1 to 6 carbon atoms. Examples of the $C_{1-6}$ alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, and an n-hexyl group.

In the present description, the term "$C_{1-4}$ alkyl group" refers to a linear or branched alkyl group containing 1 to 4 carbon atoms. Examples of the $C_{1-4}$ alkyl group include a methyl group, an ethyl group, an n-propyl group, an isopropyl group, an n-butyl group, an isobutyl group, a sec-butyl group, and a tert-butyl group.

In the present description, examples of the "$C_{1-6}$ alkoxy group" include a methoxy group, an ethoxy group, an n-propoxy group, an isopropoxy group, an n-butoxy group, an isobutoxy group, a sec-butoxy group, a tert-butoxy group, an n-pentoxy group, an isopentoxy group, a neopentoxy group, an n-hexyloxy group, and an isohexyloxy group.

In the present description, examples of the "$C_{1-4}$ alkoxy group" include a methoxy group, an ethoxy group, an n-propoxy group, an isopropoxy group, an n-butoxy group, an isobutoxy group, a sec-butoxy group, and a tert-butoxy group.

In the present description, the term "$C_{1-6}$ alkylamino group" refers to a group in which single $C_{1-6}$ alkyl group described above being bonded to a nitrogen atom. Examples of the $C_{1-6}$ alkylamino group include a methylamino group, an ethylamino group, an n-propylamino group, an isopropylamino group, a butylamino group, a sec-butylamino group, a tert-butylamino group, an n-pentylamino group, an isopentylamino group, a neopentylamino group, an n-hexylamino group, and an isohexylamino group.

In the present description, the term "$C_{1-4}$ alkylamino group" refers to a group in which single $C_{1-4}$ alkyl group described above being bonded to a nitrogen atom. Examples of the $C_{1-4}$ alkylamino group include a methylamino group, an ethylamino group, an n-propylamino group, an isopropylamino group, a butylamino group, a sec-butylamino group, and a tert-butylamino group.

In the present description, the term "N—$C_{1-6}$ alkylcarbamoyl group" refers to a carbamoyl group with single $C_{1-6}$ alkyl group described above bonded to a nitrogen atom. Examples of the N—$C_{1-6}$ alkylcarbamoyl group include an N-methylcarbamoyl group, an N-ethylcarbamoyl group, an N-n-propylcarbamoyl group, an N-isopropylcarbamoyl group, an N-butylcarbamoyl group, an N-sec-butylcarbamoyl group, an N-tert-butylcarbamoyl group, an N-n-pentylcarbamoyl group, an N-isopentylcarbamoyl group, an N-neopentylcarbamoyl group, an N-n-hexylcarbamoyl group, and an N-isohexylcarbamoyl group.

In the present description, the term "N—$C_{1-4}$ alkylcarbamoyl group" refers to a carbamoyl group with single $C_{1-4}$ alkyl group described above bonded to a nitrogen atom. Examples of the N—$C_{1-4}$ alkylcarbamoyl group include an N-methylcarbamoyl group, an N-ethylcarbamoyl group, an N-n-propylcarbamoyl group, an N-isopropylcarbamoyl group, an N-butylcarbamoyl group, an N-sec-butylcarbamoyl group, and an N-tert-butylcarbamoyl group.

In the formula (1), preferred examples of the thiazolyl group, pyridyl group, pyrazyl group, or pyrazolyl group as ring A include groups represented by the following formulae:

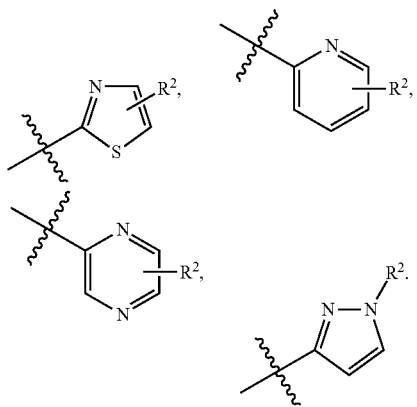

In the formula (1), the $C_{1-6}$ alkyl group as $R^1$ is preferably a $C_{1-4}$ alkyl group, and more preferably a methyl group.

In the formula (1), the hydroxy $C_{1-6}$ alkyl group as $R^1$ is preferably a hydroxy $C_{1-4}$ alkyl group, and more preferably a hydroxymethyl group.

In the formula (1), the $C_{1-6}$ alkoxy group as $R^1$ is preferably a $C_{1-4}$ alkoxy group, and more preferably a methoxy group or a tert-butoxy group.

In the formula (1), the $C_{1-6}$ alkylamino group as $R^1$ is preferably a $C_{1-4}$ alkylamino group, more preferably a methylamino group, an ethylamino group, an n-propylamino group, or an isopropylamino group, and particularly preferably a methylamino group, an ethylamino group, or an n-propylamino group.

In the formula (1), the N—$C_{1-6}$ alkylcarbamoyl group as $R^1$ is preferably an N—$C_{1-4}$ alkylcarbamoyl group, and more preferably an N-methylcarbamoyl group.

In the formula (1), preferred examples of the halogen atom as $R^2$ include a fluorine atom and a chlorine atom.

In the formula (1), the $C_{1-6}$ alkyl group as $R^2$ is preferably a $C_{1-4}$ alkyl group, and more preferably a methyl group.

In the formula (1), the $C_{1-6}$ alkoxy group as $R^2$ is preferably a $C_{1-4}$ alkoxy group, and more preferably a methoxy group.

In the formula (1), the $C_{1-6}$ alkyl group as $R^3$ is preferably a $C_{1-4}$ alkyl group, and more preferably a methyl group.

More preferred examples of the phenylacetamide compound represented by the formula (1) include compounds selected from the following group.

(S)-tert-butyl 3-((R)-2-(4-(cyclopropylsulfonyl)phenyl)-3-((5-fluorothiazol-2-yl)amino)-3-oxopropyl)pyrrolidine-1-carboxylate (Example 1), (S)-3-((R)-2-(4-(cyclopropylsulfonyl)phenyl)-3-((5-fluorothiazol-2-yl)amino)-3-oxopropyl)-N-methylpyrrolidine-1-carboxamide (Example 2), (R)-3-((S)-1-acetylpyrrolidin-3-yl)-2-(4-(cyclopropylsulfonyl)phenyl)-N-(5-fluorothiazol-2-yl)propanamide (Example 3), (S)-3-((R)-2-(4-(cyclopropylsulfonyl)phenyl)-3-((5-fluorothiazol-2-yl)amino)-3-oxopropyl)pyrrolidine-1-carboxamide (Example 4), (S)-3-((R)-2-(4-(cyclopropylsulfonyl)phenyl)-3-((5-fluorothiazol-2-yl)amino)-3-oxopropyl)-N-ethylpyrrolidine-1-carboxamide (Example 5), (S)-3-((R)-2-(4-(cyclopropylsulfonyl)phenyl)-3-((5-fluorothiazol-2-yl)amino)-3-oxopropyl)-N-propylpyrrolidine-1-carboxamide (Example 6), (S)-methyl 3-((R)-2-(4-(cyclopropylsulfonyl)phenyl)-3-((5-fluorothiazol-2-yl)amino)-3-oxopropyl)pyrrolidine-1-carboxylate (Example 7), (R)-2-(4-(cyclopropylsulfonyl)phenyl)-N-(5-fluorothiazol-2-yl)-3-((S)-1-(methylcarbamothioyl)pyrrolidin-3-yl)propanamide (Example 8), (R)-2-(4-(cyclopropylsulfonyl)phenyl)-N-(5-fluorothiazol-2-yl)-3-((S)-1-(methylsulfonyl)pyrrolidin-3-yl)propanamide (Example 9), (S)-3-((R)-2-(4-(cyclopropylsulfonyl)phenyl)-3-((5-fluorothiazol-2-yl)amino)-3-oxopropyl)-N-hydroxypyrrolidine-1-carboxamide (Example 10), (R)-2-(4-(cyclopropylsulfonyl)phenyl)-N-(5-fluorothiazol-2-yl)-3-((S)-1-(methylamino)-2-oxoacetyl)pyrrolidin-3-yl)propanamide (Example 11), (S)—N-((1-acetylazetidin-3-yl)methyl)-3-((R)-2-(4-(cyclopropylsulfonyl)phenyl)-3-((5-fluorothiazol-2-yl)amino)-3-oxopropyl)pyrrolidine-1-carboxamide (Example 12), (R)-2-(4-(cyclopropylsulfonyl)phenyl)-N-(5-fluorothiazol-2-yl)-3-((S)-1-(2-hydroxyacetyl)pyrrolidin-3-yl)propanamide (Example 13), (S)-3-((R)-2-(4-(cyclopropylsulfonyl)phenyl)-3-((5-methoxythiazol-2-yl)amino)-3-oxopropyl)-N-methylpyrrolidine-1-carboxamide (Example 14), (S)-3-((R)-3-((5-chlorothiazol-2-yl)amino)-2-(4-(cyclopropylsulfonyl)phenyl)-3-oxopropyl)-N-methylpyrrolidine-1-carboxamide (Example 15), (S)-3-((R)-2-(4-(cyclopropylsulfonyl)phenyl)-3-((5-methylthiazol-2-yl)amino)-3-oxopropyl)-N-methylpyrrolidine-1-carboxamide (Example 16), (S)-3-((R)-2-(4-(cyclopropylsulfonyl)phenyl)-3-((5-methylpyrazin-2-yl)amino)-3-oxopropyl)-N-methylpyrrolidine-1-carboxamide (Example 17), (S)-3-((R)-2-(4-(cyclopropylsulfonyl)phenyl)-3-((1-methyl-1H-pyrazol-3-yl)amino)-3-oxopropyl)-N-methylpyrrolidine-1-carboxamide (Example 18), (S)-3-((R)-2-(4-(cyclopropylsulfonyl)phenyl)-3-((5-methylpyridin-2-yl)amino)-3-oxopropyl)-N-methylpyrrolidine-1-carboxamide (Example 19), 6-((R)-2-(4-(cyclopropylsulfonyl)phenyl)-3-((S)-1-(methylcarbamoyl)pyrrolidin-3-yl)propanamido)nicotinic acid (Example 20), (S)-3-((R)-2-(4-(cyclopropylsulfonyl)phenyl)-3-((5-methylpyridin-2-yl)amino)-3-oxopropyl)pyrrolidine-1-carboxamide (Example 21), (S)-3-((R)-2-(4-(cyclopropylsulfonyl)phenyl)-3-((5-methylpyridin-2-yl)amino)-3-oxopropyl)-N-ethylpyrrolidine-1-carboxamide (Example 22), (R)-3-((S)-1-acetylpyrrolidin-3-yl)-2-(4-(cyclopropylsulfonyl)phenyl)-N-(5-methylpyridin-2-yl)propanamide (Example 23),
6-((R)-3-((S)-1-acetylpyrrolidin-3-yl)-2-(4-(cyclopropylsulfonyl)phenyl)propanamido)nicotinic acid (Example 24),
6-((R)-2-(4-(cyclopropylsulfonyl)phenyl)-3-((S)-1-(ethylcarbamoyl)pyrrolidin-3-yl)propanamido)nicotinic acid (Example 25),
(R)-3-((S)-1-acetylpyrrolidin-3-yl)-2-(4-(cyclopropylsulfonyl)phenyl)-N-(5-methoxythiazol-2-yl)propanamide (Example 26), and
2-((R)-3-((S)-1-acetylpyrrolidin-3-yl)-2-(4-(cyclopropylsulfonyl)phenyl)propanamido)thiazole-5-carboxylic acid (Example 27).

If the compound of the present invention has geometric isomers or optical isomers, such isomers are also included in the scope of the present invention. These isomers are separated according to an ordinary method.

The salt of the compound represented by the formula (1) is not particularly limited, as long as it is a pharmaceutically acceptable salt. When the compound is treated as an acidic compound, examples of the salt of the compound represented by the formula (1) include: salts with alkaline metals or alkaline-earth metals, such as sodium, potassium, magnesium, or calcium; and salts with organic bases such as trimethylamine, triethylamine, pyridine, picoline, N-methylpyrrolidine, N-methylpiperidine, or N-methylmorpholine. When the compound is treated as a basic compound, examples of the salt of the compound represented by the formula (1) include: acid-added salts with mineral acids, such as hydrochloride, hydrobromide, hydroiodide, sulfate, nitrate, or phosphate; and acid-added salts with organic acids, such as benzoate, methanesulfonate, ethanesulfonate, benzenesulfonate, p-toluenesulfonate, maleate, fumarate, tartrate, citrate, or acetate.

An example of the solvate of the compound represented by the formula (1) or a salt thereof is a hydrate. However, examples of the solvate are not limited thereto.

It is to be noted that a compound that is metabolized in a living body and is converted to the compound represented by the formula (1), namely, a prodrug is also included in the present invention. Examples of a group capable of forming the prodrug of the compound of the present invention include groups described in "Progress in Medicine," Lifescience Medica, 1985, Vol. 5, pp. 2157-2161, and groups described in "*Iyakuhin no Kaihatsu* (Development of Pharmaceutical Products)," Hirokawa Shoten, 1990, Vol. 7, *Bunshi Sekkei* (Molecular Designing), pp. 163-198.

The above described compound represented by the formula (1), or a salt thereof, or a solvate of the compound or the salt can be produced by various known methods. The production method is not particularly limited, and they can be produced, for example, according to reaction steps as described below. In addition, upon performing the following reactions, functional groups other than those in the reaction site may previously be protected as necessary, and they may be then deprotected at a suitable stage. Such protection and deprotection can be carried out with reference of commonly used methods (e.g. the method described in Protective Groups in Organic Synthesis Third Edition, John Wiley & Sons, Inc., 1999). Further, reactions in individual steps may be carried out by ordinary methods (e.g. the method described in Comprehensive Organic Transformations Second Edition, John Wiley & Sons, Inc.; 1999), and isolation and purification may be carried out by an ordinary method appropriately selected from crystallization, recrystallization, chromatography, and the like, or by a combination thereof.

(Method for Producing the Compound Represented by the Formula (1))

The compound represented by the formula (1) of the present invention can be produced by the method illustrated in reaction pathway diagram 1 as shown below. Specifically, an amide compound represented by formula (5) can be obtained by reacting a compound represented by formula (3) with an amino-heteroaryl derivative represented by formula (4). An amine compound represented by formula (6) can be obtained by removing protecting group from the amide compound represented by formula (5). A reaction reagent (7) is to react with the amine compound represented by formula (6), so as to produce the compound represented by the formula (1) of the present invention.

[Reaction Pathway Diagram 1]

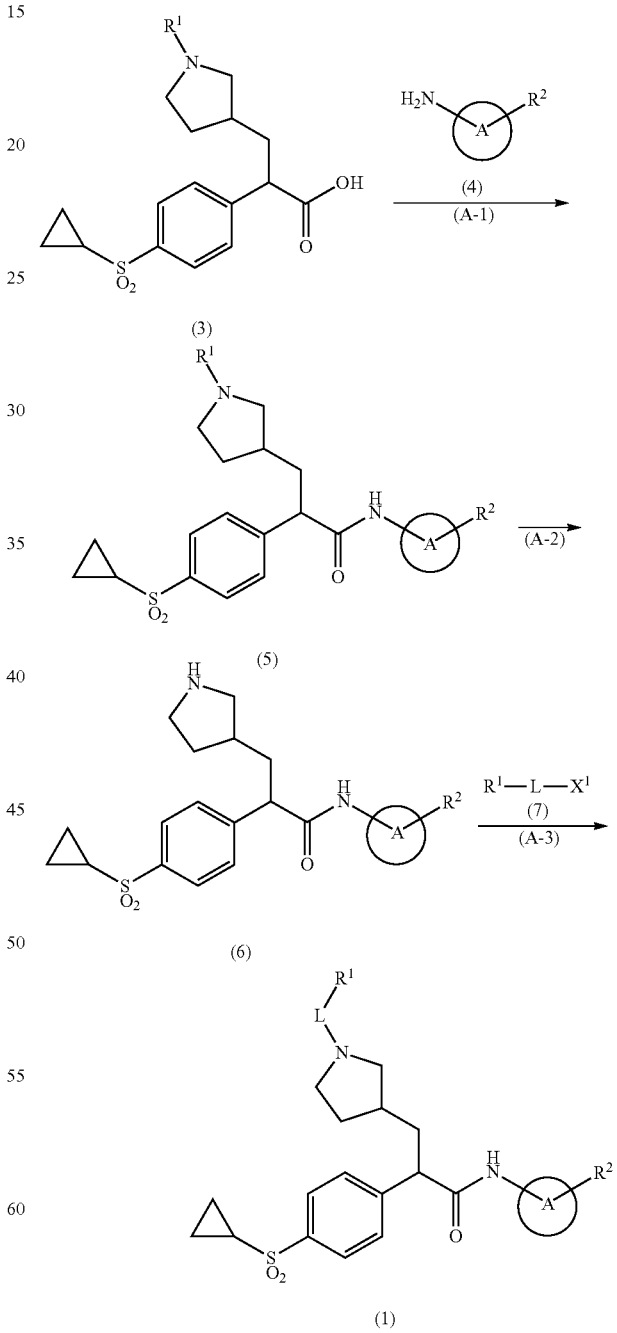

(wherein $R^1$, $R^2$, ring A, and L have the same definitions as those in the above described formula (1), $P^1$ represents a protecting group for the amino group (a benzyl group, a benzyloxycarbonyl group, a tert-butoxycarbonyl group, etc.), and $X^1$ represents a leaving group (a halogen atom etc.)).

(A-1) Step A-1 is a step of producing the compound (5) by reacting the compound (3) with the amine compound (4) in the presence of a condensing reagent. Examples of the condensing reagent used herein are not particularly limited, but include N,N'-dicyclohexylcarbodiimide (DCC), 1-ethyl-3-(3'-dimethylaminopropyl)carbodiimide hydrochloride (WSC), 2-(7-aza-1H-benzotriazol-1-yl)-1,1,3,3-tetramethyluronium hexafluoro-phosphate (HATU), 1,1'-carbonyldiimidazole (CDI), diphenylphosphoryl azide (DPPA), phosphorus oxychloride/pyridine, and triphenylphosphine/N-bromosuccinimide. In some cases, examples of an additive used herein include N-hydroxysuccinimide (HONSu) and 1-hydroxybenzotriazole hydrate (HOBt.$H_2O$). A preferred example of the condensing reagent and the additive used herein is a combination of 1-ethyl-3-(3'-dimethylaminopropyl)carbodiimide hydrochloride (WSC) and 1-hydroxybenzotriazole hydrate (HOBt.$H_2O$). Examples of the solvent used herein are not particularly limited, but include organic solvents such as N,N-dimethylformamide, tetrahydrofuran, dioxane, cyclopentylmethyl ether, dichloromethane, or dichloroethane. Of these, dichloromethane is preferable. The reaction temperature is −30° C. to 150° C., and preferably 0° C. to 100° C. The reaction time is 1 minute to 48 hours, and preferably 30 minutes to 24 hours.

(A-2) Step A-2 is a step of producing the compound (6) by removing the protecting group $P^1$ from the compound (5) obtained in Step A-1. Methods and conditions for such deprotection vary depending on the type of the protecting group $P^1$. For example, a benzyl group and a benzyloxycarbonyl group can be removed by catalytic hydrogenation, and a tert-butoxycarbonyl group can be removed by using acid. Such deprotection can be carried out with reference of a method commonly used in organic chemistry (e.g. the method described in Protective Groups in Organic Synthesis Third Edition, John Wiley & Sons, Inc., 1999).

(A-3) Step A-3 is a step of producing the compound (1) by reacting the compound (6) obtained in Step A-2 with the reaction reagent (7). In the present step, reaction such as a condensation reaction with a carboxylic acid compound, acylation with an acid chloride compound, carbamation with a chloroformic acid compound, sulfonamidation with a sulfonyl chloride compound, or a ureation reaction with a ureation reagent are available, and the reaction can be carried out with reference of an ordinary method (e.g. the method described in Comprehensive Organic Transformations Second Edition, John Wiley & Sons, Inc.; 1999).

The raw material compound represented by formula (3) can be produced by the method illustrated in reaction pathway diagram 2 as shown below. Specifically, the compound represented by formula (10) can be obtained by reacting the compound represented by formula (8) with the compound represented by formula (9). The sulfone compound represented by formula (11) can be obtained by oxidizing the sulfide compound represented by the formula (10). The protecting group $P^2$ of the ester compound represented by the formula (11) is to be removed, so as to produce the raw material compound represented by the formula (3).

[Reaction Pathway Diagram 2]

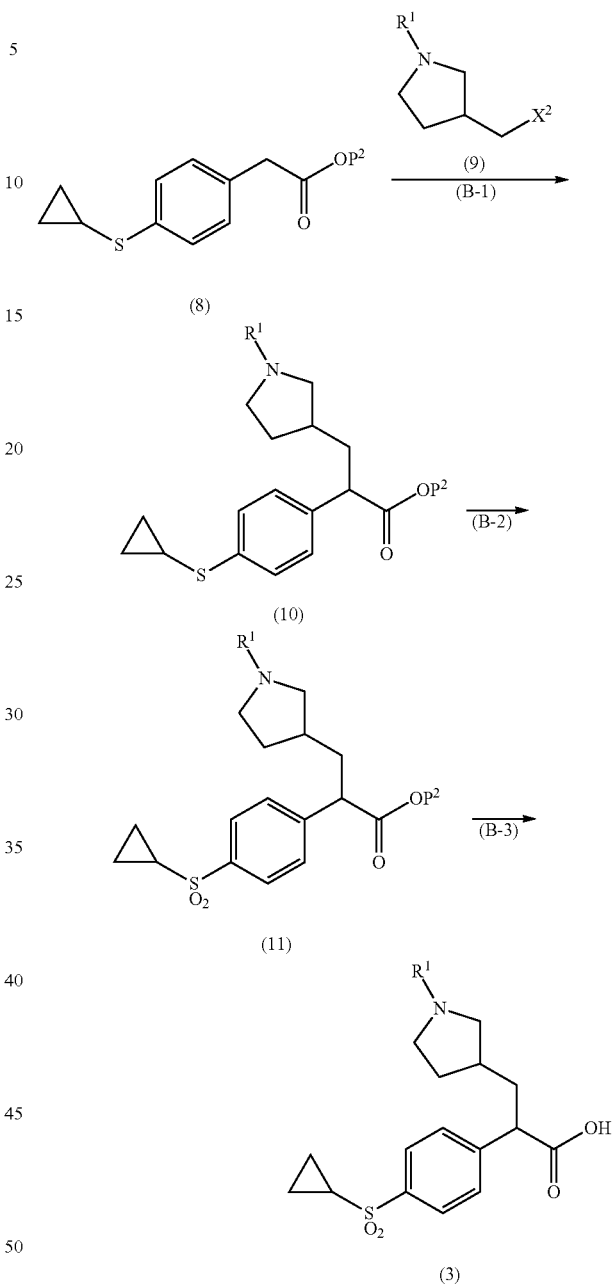

(wherein $X^2$ represents a leaving group, $P^1$ represents the same group as described above, and $P^2$ represents a protecting group for the carboxyl group).

(B-1) Step B-1 is a step of producing the compound (10) by reacting the compound (8) with the compound (9) under alkylation reaction condition. The reaction can be carried out according to a general alkylation reaction method. Examples of the base used herein are not particularly limited, but include lithium hydride, sodium hydride, potassium hydride, lithium diisopropylamide, sodium diisopropylamide, potassium diisopropylamide, lithium hexamethyldisilazide, sodium hexamethyldisilazide, potassium hexamethyldisilazide, sodium tert-butoxide, potassium tert-butoxide, n-butyllithium, sec-butyllithium, and tert-butyllithium. Of these, lithium diisopropylamide is preferable. Examples of the solvent used herein are not particularly limited, but include organic solvents such as diethyl ether, tetrahydrofuran, dioxane, cyclopentylmethyl ether, dimethoxyethane, or 1,3-dimethyl-3,4,5,6-tetrahydro-2(1H)-pyrimidinone. These solvents can be used either singly or in combination. A mixed solvent of tetrahydrofuran and 1,3-dimethyl-3,4,5,6-tetrahydro-2(1H)-pyrimidinone is preferable. The reaction temperature is −150° C. to 100° C., and preferably −100° C. to 50° C. The reaction time is 1 minute to 48 hours, and preferably 30 minutes to 24 hours.

(B-2) Step B-2 is a step of producing the compound (11) by oxidizing the compound (10). Examples of the oxidizing agent used herein are not particularly limited, but include hydrogen peroxide solution, peracetic acid, pertrifluoroacetic acid, dimethyl dioxirane, Oxone®, meta-chloroperbenzoic acid, magnesium bis(peroxyphthalate) hexahydrate, potassium permanganate, and chromium(VI) oxide. Of these, m-chloroperbenzoic acid is preferable. Examples of the solvent used herein are not particularly limited, but include dichloromethane, dichloroethane, and chloroform. Of these, dichloromethane is preferable. The reaction temperature is −30° C. to 50° C., and preferably −10° C. to 30° C. The reaction time is 5 minutes to 40 hours, and preferably 10 minutes to 24 hours.

(B-3) Step B-3 is a step of producing the compound (3) by hydrolyzing the compound (11). Examples of the base used herein are not particularly limited, but include alkali metal hydroxides such as lithium hydroxide, sodium hydroxide, or potassium hydroxide. Of these, sodium hydroxide is preferable. Examples of the solvent used herein are not particularly limited, but include methanol, ethanol, isopropanol, tetrahydrofuran, and dioxane. These solvents can be used either singly or in combination. Among these solvents, ethanol is preferable. The reaction temperature is −30° C. to 50° C., and preferably −10° C. to 30° C. The reaction time is 5 minutes to 10 hours, and preferably 10 minutes to 5 hours.

It is to be noted that the compound (8) used as a raw material can be produced by a method described in known methods (WO2008/111473 etc.) or a method similar thereto.

The raw material compound represented by formula (9) can be produced by the method illustrated in reaction pathway diagram 3 as shown below. Specifically, the raw material compound represented by the formula (9) can be produced by activating a hydroxyl group of the compound represented by formula (12).

[Reaction Pathway Diagram 3]

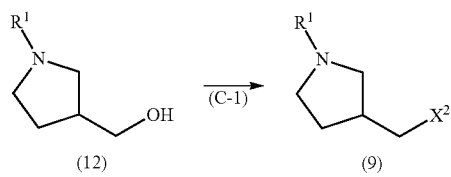

(wherein $P^2$ and $X^2$ represent the same groups as described above).

(C-1) Step C-1 is a step of producing the raw material compound represented by the formula (9) by subjecting a hydroxyl group of the compound (12) to halogenation or sulfonylation in the presence or absence of a base. Examples of the reagent used herein are not particularly limited, but include phosphorus trichloride, phosphorus tribromide, carbon tetrachloride/triphenylphosphine, carbon tetrabromide/triphenylphosphine, triphenylphosphine/iodine, methane sulfonyl chloride, 4-toluenesulfonyl chloride, and trifluoromethanesulfonic anhydride. Of these, triphenylphosphine/iodine is preferable. Examples of the base used herein are not particularly limited, but include imidazole, 1,8-diazabicyclo[5.4.0]undec-7-ene (DBU), 1,5-diazabicyclo[4.3.0]non-5-ene (DBN), DABCO, triethylamine, N,N-diisopropylethylamine, N,N-diisopropylpentylamine, trimethylamine, pyridine, and 2,6-lutidine. Of these, imidazole is preferable. Examples of the solvent used herein are not particularly limited, but include dichloromethane, tetrahydrofuran, and dioxane. Of these, dichloromethane is preferable. The reaction temperature is −30° C. to 50° C., and preferably −10° C. to 30° C. The reaction time is 5 minutes to 30 hours, and preferably 10 minutes to 20 hours.

It is to be noted that the compound (12) used as a raw material can be produced by the method described in known methods (Bioorg. Med. Chem. Lett., 19, 2829-2834 (2009) etc.) or a method similar thereto.

Reaction intermediates and products of interest, which were obtained from each of the above described reactions, can be isolated and purified, as necessary, by applying purification methods commonly used in organic synthetic chemistry, such as filtration, extraction, washing, drying, concentration, recrystallization, or various types of chromatography. In addition, in the case of reaction intermediates, they can also be subjected to the subsequent reaction without being particularly purified.

Moreover, various types of isomers can be isolated by applying a general method which utilizes differences in physicochemical properties among the isomers. A racemic mixture can be induced to an optically pure isomer by a common racemic resolution method, such as a method which comprises inducing a racemic mixture to diastereomeric salts with common optically active acid such as tartaric acid and then subjecting the salts to optical resolution, or a method using optically active column chromatography. Furthermore, a diastereomeric mixture can be divided, for example, by fractional crystallization or various types of chromatography. Further, an optically active compound can also be produced by using suitable optically active raw materials.

The obtained compound (1) can be converted to salts according to an ordinary method. In addition, it can also be converted to a solvate in solvents such as a reaction solvent or a recrystallization solvent, or a hydrate.

As a pharmaceutical preparation comprising, as an active ingredient, the compound represented by the formula (1) of the present invention, or a salt thereof, or a solvate of the compound or the salt, the aforementioned active ingredient may be used singly. However, in general, pharmaceutically acceptable carriers, additives, and the like are mixed with the active ingredient, and the thus obtained mixture is used as a pharmaceutical preparation. The dosage form of a pharmaceutical composition is not particularly limited, and it can be selected, as appropriate, depending on therapeutic purpose. For example, the dosage form may be any one of an oral agent, an injection, a suppository, an ointment, an inhalant, eye drops, nasal drops, and a patch. A pharmaceutical composition suitable for each of these dosage forms can be produced by known pharmaceutical formulation methods.

In the case of preparing a solid preparation for oral administration, an excipient, and as necessary, a binder, a disintegrator, a lubricant, a coloring agent, a corrigent, a flavoring agent, and the like are added to the compound represented by the formula (1), and thereafter, a tablet, a coated tablet, a granule, a powder agent, a capsule, and the like can be produced from the obtained mixture according to an ordinary method. Additives commonly used in the present technical field can be used herein. Examples of the excipient used herein include lactose, saccharose, sodium chloride, glucose, starch, calcium carbonate, kaoline, microcrystalline cellulose, and silicic acid. Examples of the binder used herein include water, ethanol, propanol, simple syrup, glucose solution, starch solution, gelatin solution, carboxymethylcellulose, hydroxypropylcellulose, hydroxypropyl starch, methylcellulose, ethylcellulose, shellac, calcium phosphate, and polyvinyl pyrrolidone. Examples of the disintegrator used herein include dry starch, sodium alginate, agar powder, sodium hydrogen carbonate, calcium carbonate, sodium lauryl sulfate, monoglyceride stearate, and lactose. Examples of the lubricant used herein include purified talc, stearate, borax, and polyethylene glycol. Examples of the corrigent used herein include saccharose, bitter orange peel, citric acid, and tartaric acid.

In the case of preparing a liquid preparation for oral administration, a corrigent, a buffer, a stabilizer, a flavoring agent, and the like are added to the compound represented by the formula (1), and thereafter, an oral liquid agent, a syrup agent, an elixir agent, and the like can be produced from the obtained mixture according to an ordinary method. Examples of the corrigent used herein are the same as those described above. An example of the buffer used herein is sodium citrate, and examples of the stabilizer used herein include tragacanth, gum Arabic, and gelatin.

In the case of preparing an injection, a pH adjuster, a buffer, a stabilizer, an isotonizing agent, a regional anesthetic, and the like are added to the compound represented by the formula (1), and thereafter, hypodermic, intramuscular and intravenous injections can be produced from the obtained mixture according to an ordinary method. Examples of the pH adjuster and buffer used herein include sodium citrate, sodium acetate, and sodium phosphate. Examples of the stabilizer used herein include sodium pyrosulfite, EDTA, thioglycolic acid, and thiolactic acid. Examples of the regional anesthetic used herein include procaine hydrochloride and lidocaine hydrochloride. Examples of the isotonizing agent used herein include sodium chloride and glucose.

In the case of preparing a suppository, known suppository carriers such as polyethylene glycol, lanolin, cacao butter, or fatty acid triglyceride, and as necessary, a surfactant such as Tween® are added to the compound represented by the formula (1), and thereafter, suppositories can be produced from the obtained mixture according to an ordinary method.

In the case of preparing an ointment, commonly used base, stabilizer, wetting agent, preservative, etc. are mixed into the compound represented by the formula (1), as necessary, and thereafter, the obtained mixture is blended to produce an ointment according to an ordinary method. Examples of the base used herein include liquid paraffin, white petrolatum, white beeswax, octyldodecyl alcohol, and paraffin. Examples of the preservative used herein include methyl p-hydroxybenzoate, ethyl p-hydroxybenzoate, and propyl p-hydroxybenzoate.

Other than the aforementioned dosage forms, the compound represented by the formula (1) can also be processed into an inhalant, eye drops, or nasal drops according to ordinary methods.

The compound represented by the formula (1) of the present invention is administered via oral administration or parenteral administration. The dose of the pharmaceutical preparation of the present invention is different depending on the body weight, age, sex, and symptoms of a patient, etc. In general, in the case of an adult patient, the compound represented by the formula (1) is preferably administered at a dose of 0.01 to 1000 mg/day, and preferably 0.1 to 300 mg/day, in one to three divided doses.

EXAMPLES

Hereinafter, the present invention will be more specifically described in the following Examples and Test Examples. However, these examples are not intended to limit the scope of the present invention. It is to be noted that abbreviations used in the following examples have the following meanings.
s: singlet
d: doublet
t: triplet
q: quartet
m: multiplet
br: broad
J: coupling constant
Hz: Hertz
$CDCl_3$: deuterated chloroform
DMSO-$d_6$: deuterated dimethyl sulfoxide
$^1$H-NMR: proton nuclear magnetic resonance
quant: quantitative Example 1

Production of (S)-tert-butyl 3-((R)-2-(4-(cyclopropylsulfonyl)phenyl)-3-((5-fluorothiazol-2-yl)amino)-3-oxopropyl)pyrrolidine-1-carboxylate Step 1: Triphenylphosphine (182.2 g, 695 mmol) and imidazole (47.4 g, 696 mmol) were dissolved in dichloromethane (1.6 L), and iodine (70.4 g, 555 mmol) was then added to the above obtained solution under ice-cold condition. The obtained mixture was stirred for 10 minutes. After that, a dichloromethane solution (200 mL) of the (S)-tert-butyl 3-(hydroxymethyl)pyrrolidine-1-carboxylate (55.8 g, 278 mmol) synthesized by a method described in the known method (Bioorg. Med. Chem. Lett., 19, 2829-2834 (2009)) was further added to the reaction solution, and the obtained mixture was then stirred at room temperature for 15 hours. Thereafter, the reaction solution was washed with an aqueous solution of sodium sulfite, was then dried over anhydrous sodium sulfate, and was then concentrated in vacuo. The obtained residue was purified by silica gel chromatography (hexane/ethyl acetate=2%→25%) to obtain (S)-tert-butyl 3-(iodomethyl)pyrrolidine-1-carboxylate (73.2 g, 85%) in the form of a colorless oily product.

$^1$H-NMR ($CDCl_3$) δ: 1.46 (9H, s), 1.64 (1H, m), 2.05 (1H, m), 2.49 (1H, m), 3.01 (1H, m), 3.19 (2H, m), 3.33 (1H, m), 3.45-3.62 (3H, m)

Step 2: A mixed solvent of 1,3-dimethyl-3,4,5,6-tetrahydro-2(1H)-pyrimidinone and tetrahydrofuran (1: 10, 220 mL) was cooled to −78° C., and lithium diisopropylamide (2.0 M tetrahydrofuran/heptane/ethyl benzene solution, 42.6 mL) was then added thereto. To the obtained solution, a mixed solvent solution (1,3-dimethyl-3,4,5,6-tetrahydro-2(1H)-pyrimidinone: tetrahydrofuran=1: 10, 200 mL) comprising the ethyl 2-(4-(cyclopropylthio)phenyl)acetate (18.5 g, 78.2 mmol) obtained by a method described in the known publication (WO2008/111473) was added dropwise over 20 minutes, and the thus obtained mixture was then stirred at the same temperature as above for 1 hour. Thereafter, a mixed solvent solution (1,3-dimethyl-3,4,5,6-tetrahydro-2(1H)-pyrimidinone: tetrahydrofuran=1: 10, 200 mL) comprising (S)-tert-butyl 3-(iodomethyl)pyrrolidine-1-carboxylate (22.2 g, 71.3 mmol) was further added dropwise to the reaction solution over 30 minutes. The obtained mixture was stirred at the same temperature as above for 1 hour, and then at room temperature for 2 hours. Thereafter, the reaction solution was cooled to 0° C., and water was then added to the reaction solution, followed by extraction with ethyl acetate. The organic layer was washed with brine, was then dried over anhydrous sodium sulfate, and was then concentrated in vacuo. The obtained residue was purified by silica gel chromatography (hexane/ethyl acetate=5%→35%) to obtain (3S)-tert-butyl 3-(2-(4-(cyclopropylthio)phenyl-3-ethoxy-3-oxopropyl)pyrrolidine-1-carboxylate (23.8 g, 80%) in the form of a white solid.

$^1$H-NMR (CDCl$_3$) δ: 0.69 (2H, m), 1.07 (2H, m), 1.22 (3H, m), 1.44 (9H, s), 1.84-2.05 (4H, m), 2.16 (1H, m), 2.83 (1H, m), 3.18 (1H, m), 3.36-3.56 (3H, m), 4.11 (2H, m), 7.23 (2H, d, J=8.5 Hz), 7.31 (2H, d, J=8.5 Hz)

Step 3: (3S)-tert-Butyl 3-(2-(4-(cyclopropylthio)phenyl-3-ethoxy-3-oxopropyl)pyrrolidine-1-carboxylate (23.8 g, 56.7 mmol) was dissolved in dichloromethane (300 mL), and a dichloromethane solution (50 mL) of meta-chloroperbenzoic acid (29.4 g, 119.3 mmol) was then added to the above obtained solution under ice-cold condition. The obtained mixture was stirred at room temperature for 19 hours. Thereafter, the reaction solution was washed with an aqueous solution of sodium sulfite, was then dried over anhydrous sodium sulfate, and was then concentrated in vacuo. The obtained residue was purified by silica gel chromatography (hexane/ethyl acetate=10%→70%) to obtain (3S)-tert-butyl 3-(2-(4-(cyclopropylsulfonyl)phenyl-3-ethoxy-3-oxopropyl)pyrrolidine-1-carboxylate (20.0 g, 78%) in the form of a white solid.

$^1$H-NMR (CDCl$_3$) δ 1.05 (2H, m), 1.22 (3H, m), 1.37 (2H, m), 1.44 (9H, s), 1.58 (1H, m), 1.84-2.04 (3H, m), 2.20 (1H, m), 2.45 (1H, m), 2.89 (1H, m), 3.21 (1H, m), 3.40-3.58 (2H, m), 3.65 (1H, m), 4.13 (2H, m), 7.51 (2H, d, J=8.5 Hz), 7.86 (2H, d, J=8.5 Hz)

Step 4: (3S)-tert-Butyl 3-(2-(4-(cyclopropylsulfonyl)phenyl-3-ethoxy-3-oxopropyl)pyrrolidine-1-carboxylate (20.0 g, 44.3 mmol) was dissolved in ethanol (110 mL), and an aqueous solution of sodium hydroxide (8 M, 22 mL) was then added to the obtained solution under ice-cold condition. The obtained mixture was stirred for 1 hour. Thereafter, the reaction solution was neutralized with a 0.5 M aqueous solution of hydrochloric acid, and was then extracted with chloroform. The organic layer was dried over anhydrous sodium sulfate, and was then concentrated in vacuo, so as to obtain 3-((S)-1-tert-butoxycarbonyl)pyrrolidin-3-yl)-2-(4-(cyclopropylsulfonyl)phenyl)propanoic acid (20.0 g, quant) in the form of a white solid.

$^1$H-NMR (DMSO-d$_6$) δ: 0.99 (2H, m), 1.09 (2H, m), 1.32 (9H, s), 1.48 (1H, m), 1.82 (3H, m), 2.03 (1H, m), 2.68 (1H, m), 2.81 (1H, m), 3.04 (1H, m), 3.25 (2H, m), 3.67 (1H, m), 7.57 (2H, d, J=8.5 Hz), 7.81 (2H, d, J=8.5 Hz)

Step 5: 3-((S)-1-tert-Butoxycarbonyl)pyrrolidin-3-yl)-2-(4-(cyclopropylsulfonyl)phenyl)propanoic acid (2.60 g, 6.14 mmol) was dissolved in tetrahydrofuran (50 mL), and thereafter, triethylamine (0.972 mL, 7.01 mmol) and pivaloyl chloride (0.891 mL, 7.32 mmol) were added to the above obtained solution under ice-cold condition. The obtained mixture was stirred for 1 hour. During this reaction, (R)-(+)-4-benzyl-2-oxazolidinone (1.30 g, 7.34 mmol) was dissolved in tetrahydrofuran (50 mL), and the obtained solution was then cooled to −78° C. Subsequently, n-butyl lithium (2.6 M hexane solution, 2.70 mL) was added to the reaction solution, and the thus obtained mixture was then stirred at room temperature for 30 minutes. The thus obtained solution was added dropwise over 10 minutes to an anhydride solution that had been cooled to −78° C., and the obtained mixture was then stirred at room temperature for 2 hours. Thereafter, water was added to the reaction solution, and the mixed solution was then extracted with ethyl acetate. The organic layer was dried over anhydrous sodium sulfate, and was then concentrated in vacuo. The obtained residue was purified by silica gel chromatography (hexane/ethyl acetate=15%→80%) to obtain (S)-tert-butyl 3-((R)-3-((R)-4-benzyl-2-oxooxazolidin-3-yl)-2-(4-(cyclopropylsulfonyl)phenyl)-3-oxopropyl)pyrrolidine-1-carboxylate (1.38 g, 38.8%) in the form of a white solid.

$^1$H-NMR (DMSO-d$_6$) δ: 1.02 (2H, m), 1.09 (2H, m), 1.37 (9H, s), 1.50 (1H, m), 1.82 (3H, m), 2.15 (1H, m), 2.89 (2H, m), 3.01 (1H, m), 3.09 (2H, m), 3.34 (1H, m), 3.40 (1H, m), 4.21 (1H, m), 4.27 (1H, m), 4.67 (1H, m), 5.06 (1H, m), 7.22-7.34 (5H, m), 7.59 (2H, d, J=8.5 Hz), 7.86 (2H, d, J=8.5 Hz)

Step 6: (S)-tert-Butyl 3-((R)-3-((R)-4-benzyl-2-oxooxazolidin-3-yl)-2-(4-(cyclopropylsulfonyl)phenyl)-3-oxopropyl)pyrrolidine-1-carboxylate (1.38 g, 2.36 mmol) was dissolved in a mixed solvent of tetrahydrofuran and water (3: 1, 12.8 mL), and an aqueous solution (1.9 mL) consisting of lithium hydroxide (113 mg, 4.72 mmol) and a hydrogen peroxide solution (30%, 1.10 mL) was added to the above obtained solution under ice-cold condition. The obtained mixture was stirred for 1 hour. Thereafter, an aqueous solution of sodium sulfite was added to the reaction solution, and the mixed solution was then washed with diethyl ether. The reaction solution was neutralized with a 0.5 M aqueous solution of hydrochloric acid, and was then extracted with ethyl acetate. The organic layer was dried over anhydrous sodium sulfate, and was then concentrated in vacuo, so as to obtain (R)-3-((S)-1-tert-butoxycarbonyl)pyrrolidin-3-yl)-2-(4-(cyclopropylsulfonyl)phenyl)propanoic acid (910 mg, 85%) in the form of a white solid.

$^1$H-NMR (DMSO-d$_6$) δ: 0.99 (2H, m), 1.09 (2H, m), 1.32 (9H, s), 1.48 (1H, m), 1.82 (3H, m), 2.03 (1H, m), 2.83 (2H, m), 3.04 (1H, m), 3.25 (2H, m), 3.67 (1H, m), 7.57 (2H, d, J=8.5 Hz), 7.81 (2H, d, J=8.5 Hz)

Step 7: (R)-3-((S)-1-tert-Butoxycarbonyl)pyrrolidin-3-yl)-2-(4-(cyclopropylsulfonyl)phenyl)propanoic acid (2.00 g, 4.72 mmol) was dissolved in dichloromethane (50 mL), and thereafter, 1-ethyl-3-(3-dimethylaminopropyl)carbodiimide hydrochloride (1.81 g, 9.44 mmol), 1-hydroxybenzotriazole hydrate (1.44 g, 9.44 mmol), and 2-amino-5-fluorothiazole (700 mg, 5.93 mmol) were added to the above obtained solution. The obtained mixture was stirred for 19 hours. Thereafter, the reaction solution was washed with water, was then dried over anhydrous sodium sulfate, and was then concentrated in vacuo. The obtained residue was purified by silica gel chromatography (chloroform/methanol=1%→15%) to obtain the captioned compound (2.57 g, quant) in the form of a white solid.

$^1$H-NMR (CDCl$_3$) δ: 1.05 (2H, m), 1.37 (2H, m), 1.45 (9H, s), 1.63 (1H, m), 1.85-2.05 (2H, m), 2.15 (1H, m), 2.47 (1H, m), 2.92 (1H, m), 3.15 (1H, m), 3.36-3.56 (2H, m), 3.72 (1H, m), 7.00 (1H, m), 7.55 (2H, m), 7.89 (2H, m)

Example 2

Production of (S)-3-((R)-2-(4-(cyclopropylsulfonyl)phenyl)-3-((5-fluorothiazol-2-yl)amino)-3-oxopropyl)-N-methylpyrrolidine-1-carboxamide Step 1: The (S)-tert-butyl 3-((R)-2-(4-(cyclopropylsulfonyl)phenyl)-3-((5-fluorothiazol-2-yl)amino)-3-oxopropyl)pyrrolidine-1-carboxylate (2.57 g, 4.91 mmol) obtained in Example 1 was dissolved in hydrochloric acid (4 M ethyl acetate solution, 10 mL), and the obtained mixture was then stirred for 10 minutes. Thereafter, the reaction solution was concentrated in vacuo, and the obtained residue was then dissolved in chloroform. The obtained solution was washed with a saturated aqueous solution of sodium hydrogen carbonate, was then dried over sodium sulfate, and was then concentrated in vacuo, so as to obtain (R)-2-(4-(cyclopropylsulfonyl)phenyl)-N-(5-fluorothiazol-2-yl)-3-((S)-pyrrolidin-3-yl)propanamide (2.26 g, quant) in the form of a white solid.

$^1$H-NMR (DMSO-d$_6$) δ: 0.99 (2H, m), 1.08 (2H, m), 1.30 (1H, m), 1.80 (3H, m), 2.13 (1H, m), 2.70-2.95 (3H, m), 3.30-3.69 (3H, m), 3.88 (1H, m), 7.09 (1H, d, J=1.8 Hz), 7.59 (2H, d, J=8.5 Hz), 7.80 (2H, d, J=8.5 Hz)

Step 2: (R)-2-(4-(Cyclopropylsulfonyl)phenyl)-N-(5-fluorothiazol-2-yl)-3-((S)-pyrrolidin-3-yl)propanamide (500 mg, 1.05 mmol) was dissolved in tetrahydrofuran (40 mL), and thereafter, phenyl N-methylcarbamate (636 mg, 4.21 mmol) and an aqueous solution of sodium hydroxide (2 M, 2 mL) were added to the above obtained solution under ice-cold condition. The obtained mixture was stirred for 1.5 hours. Thereafter, water was added to the reaction solution, and the mixed solution was then extracted with ethyl acetate. The organic layer was dried over anhydrous sodium sulfate, and was then concentrated in vacuo. The obtained residue was purified by silica gel chromatography (chloroform/methanol=1%→15%) to obtain the captioned compound (377 mg, 75%) in the form of a white solid.

$^1$H-NMR (DMSO-d$_6$) δ: 0.99 (2H, m), 1.07 (2H, m), 1.46 (1H, m), 1.72-1.90 (3H, m), 2.08 (1H, m), 2.46 (3H, d, J=4.6 Hz), 2.80 (2H, m), 3.03 (1H, m), 3.22 (1H, m), 3.32 (1H, m), 3.95 (1H, m), 5.89 (1H, d, J=4.6 Hz), 7.26 (1H, d, J=1.8 Hz), 7.60 (2H, d, J=8.7 Hz), 7.84 (2H, d, J=8.7 Hz).

Example 3

Production of (R)-3-((S)-1-acetylpyrrolidin-3-yl)-2-(4-(cyclopropylsulfonyl)phenyl)-N-(5-fluorothiazol-2-yl)propanamide The (R)-2-(4-(cyclopropylsulfonyl)phenyl)-N-(5-fluorothiazol-2-yl)-3-((S)-pyrrolidin-3-yl)propanamide (1.17 g, 2.77 mmol) obtained in Step 1 of Example 2 was dissolved in dichloromethane (27 mL), and thereafter, triethylamine (0.806 mL, 5.81 mmol) and acetyl chloride (0.207 mL, 2.91 mmol) were added to the above obtained solution under ice-cold condition. The obtained mixture was stirred for 20 minutes. Thereafter, the reaction solution was washed with a 1 M aqueous solution of hydrochloric acid and a saturated aqueous solution of sodium hydrogen carbonate. The resultant was dried over anhydrous sodium sulfate, and was then concentrated in vacuo. The obtained residue was purified by silica gel chromatography (chloroform/methanol=1%→15%) to obtain the captioned compound (980 mg, 76%) in the form of a white solid.

$^1$H-NMR (DMSO-d$_6$) δ: 0.95-1.10 (4H, m), 1.40-1.68 (1H, m), 1.70-1.98 (6H, m), 2.02-2.22 (1H, m), 2.80 (2H, m), 3.03 (1H, m), 3.21-3.57 (2H, m), 3.97 (1H, m), 7.27 (1H, m), 7.61 (2H, m), 7.84 (2H, m).

Example 4

Production of (S)-3-((R)-2-(4-(cyclopropylsulfonyl)phenyl)-3-((5-fluorothiazol-2-yl)amino)-3-oxopropyl)pyrrolidine-1-carboxamide The (R)-2-(4-(cyclopropylsulfonyl)phenyl)-N-(5-fluorothiazol-2-yl)-3-((S)-pyrrolidin-3-yl)propanamide (20.0 mg, 47.2 μmol) obtained in Step 1 of Example 2 was dissolved in dichloromethane (1 mL), and trimethylsilyl isocyanate (25.0 μL, 188 μmol) was then added to the obtained solution. The obtained mixture was stirred for hours. Thereafter, water was added to the reaction solution, and the mixed solution was then extracted with chloroform. The organic layer was dried over anhydrous sodium sulfate, and was then concentrated in vacuo. The obtained residue was purified by silica gel chromatography (chloroform/methanol=1%→20%) to obtain the captioned compound (22.0 mg, 99%) in the form of a white solid.

$^1$H-NMR (CDCl$_3$) δ: 1.03 (2H, m), 1.36 (2H, m), 1.65-1.92 (3H, m), 2.10 (1H, m), 2.54 (2H, m), 3.14 (2H, m), 3.32 (1H, m), 3.86 (1H, m), 4.17 (1H, m), 5.81 (2H, br), 6.87 (1H, d, J=1.8 Hz), 7.72 (2H, d, J=8.2 Hz), 7.92 (2H, d, J=8.2 Hz).

Example 5

Production of (S)-3-((R)-2-(4-(cyclopropylsulfonyl)phenyl)-3-((5-fluorothiazol-2-yl)amino)-3-oxopropyl)-N-ethylpyrrolidine-1-carboxamide The captioned compound was obtained in the form of a white solid by performing the same reaction and treatment as those in Example 4, with the exception that ethyl isocyanate was used instead of trimethylsilyl isocyanate.

$^1$H-NMR (CDCl$_3$) δ: 0.99-1.18 (5H, m), 1.36 (2H, m), 1.55-1.67 (1H, m), 1.86-2.25 (4H, m), 2.47 (1H, m), 3.10-3.20 (3H, m), 3.36 (1H, m), 3.56 (1H, m), 3.82 (1H, m), 4.15 (1H, m), 6.97 (1H, s), 7.58 (2H, d, J=8.3 Hz), 7.89 (2H, d, J=8.3 Hz).

Example 6

Production of (S)-3-((R)-2-(4-(cyclopropylsulfonyl)phenyl)-3-((5-fluorothiazol-2-yl)amino)-3-oxopropyl)-N-propylpyrrolidine-1-carboxamide The captioned compound was obtained in the form of a white solid by performing the same reaction and treatment as those in Example 4, with the exception that propyl isocyanate was used instead of trimethylsilyl isocyanate.

$^1$H-NMR (DMSO-d$_6$) δ: 0.79 (3H, t, J=7.3 Hz), 1.03 (2H, m), 1.11 (2H, m), 1.42 (2H, dd, J=7.3, 14.4 Hz), 1.50 (1H, m), 1.80-1.98 (2H, m), 2.13 (1H, m), 2.85 (1H, m), 2.90 (1H, m), 3.10 (1H, m), 3.26-3.80 (4H, m), 4.00 (1H, m), 5.99 (1H, t, J=4.2 Hz), 7.30 (1H, d, J=1.8 Hz), 7.64 (2H, d, J=8.5 Hz), 7.88 (2H, d, J=8.5 Hz).

Example 7

Production of (S)-methyl 3-((R)-2-(4-(cyclopropylsulfonyl)phenyl)-3-((5-fluorothiazol-2-yl)amino)-3-oxopropyl)pyrrolidine-1-carboxylate The captioned compound was obtained in the form of a white solid by performing the same reaction and treatment as those in Example 3, with the exception that methyl chloroformate was used instead of acetyl chloride.

$^1$H-NMR (CDCl$_3$) δ: 1.07 (2H, m), 1.38 (2H, m), 1.87-2.36 (5H, m), 2.47 (1H, m), 2.91-3.10 (1H, m), 3.23 (1H, m), 3.39-3.75 (3H, m), 3.69 (3H, s), 6.98 (1H, s), 7.54 (2H, d, J=7.8 Hz), 7.90 (2H, d, J=7.8 Hz).

Example 8

Production of (R)-2-(4-(cyclopropylsulfonyl)phenyl)-N-(5-fluorothiazol-2-yl)-3-((S)-1-(methylcarbamothioyl)pyrrolidin-3-yl)propanamide The captioned compound was obtained in the form of a white solid by performing the same reaction and treatment as those in Example 4, with the exception that methyl thioisocyanate was used instead of trimethylsilyl isocyanate.

$^1$H-NMR (CDCl$_3$) δ: 1.03 (2H, m), 1.31 (2H, m), 1.61 (1H, m), 2.05 (3H, m), 2.20 (1H, m), 2.47 (1H, m), 3.10 (3H, s), 3.21 (1H, m), 3.35 (1H, m), 3.72 (2H, m), 3.85 (1H, m), 5.56 (1H, s), 6.98 (1H, d, J=1.8 Hz), 7.51 (2H, d, J=8.5 Hz), 7.81 (2H, d, J=8.5 Hz)

Example 9 Production of (R)-2-(4-(cyclopropylsulfonyl)phenyl)-N-(5-fluorothiazol-2-yl)-3-((S)-1-(methylsulfonyl)pyrrolidin-3-yl)propanamide The captioned compound was obtained in the form of a white solid by performing the same reaction and treatment as those in Example 3, with the exception that methanesulfonyl chloride was used instead of acetyl chloride.

$^1$H-NMR (CDCl$_3$) δ: 1.03 (2H, m), 1.32 (2H, m), 1.59 (1H, m), 2.02 (3H, m), 2.23 (1H, m), 2.47 (1H, m), 2.82 (3H, s), 2.96 (1H, m), 3.18 (1H, m), 3.43 (2H, m), 3.75 (1H, m), 6.97 (1H, d, J=1.8 Hz), 7.48 (2H, d, J=8.5 Hz), 7.81 (2H, d, J=8.5 Hz)

Example 10

Production of (S)-3-((R)-2-(4-(cyclopropylsulfonyl)phenyl)-3-((5-fluorothiazol-2-yl)amino)-3-oxopropyl)-N-hydroxypyrrolidine-1-carboxamide The (R)-2-(4-(cyclopropylsulfonyl)phenyl)-N-(5-fluorothiazol-2-yl)-3-((S)-pyrrolidin-3-yl)propanamide (39.1 mg, 92.3 μmol) obtained in Step 1 of Example 2 was dissolved in ethanol (2 mL), and phenyl N-hydroxycarbamate (56.0 mg, 366 μmol) was then added to the obtained solution. The obtained mixture was stirred for 5 hours at reflux. Thereafter, water was added to the reaction solution, and the mixed solution was then extracted with chloroform. The organic layer was dried over anhydrous sodium sulfate, and was then concentrated in vacuo. The obtained residue was purified by silica gel chromatography (chloroform/methanol=1%→20%) to obtain the captioned compound (24.2 mg, 54%) in the form of a white solid.

$^1$H-NMR (CDCl$_3$) δ: 1.05 (2H, m), 1.36 (2H, m), 1.75 (2H, m), 1.92 (1H, m), 2.10 (1H, m), 2.50 (1H, m), 2.58 (1H, m), 3.14 (1H, m), 3.28 (2H, m), 3.84 (1H, m), 4.32 (1H, m), 6.88 (1H, d, J=1.8 Hz), 7.69 (2H, d, J=8.5 Hz), 7.88 (2H, d, J=8.5 Hz)

Example 11

Production of (R)-2-(4-(cyclopropylsulfonyl)phenyl)-N-(5-fluorothiazol-2-yl)-3-((S)-1-(methylamino)-2-oxoacetyl)pyrrolidin-3-yl)propanamide Step 1: Ethyl 2-((S)-3-((R)-2-(4-(cyclopropylsulfonyl)phenyl)-3-((5-fluorothiazol-2-yl)amino)-3-oxopropyl)pyrrolidin-1-yl)-2-oxoacetate was obtained in the form of a white solid by performing the same reaction and treatment as those in Example 3, with the exception that ethyl chlorooxoacetate was used instead of acetyl chloride.

$^1$H-NMR (CDCl$_3$) δ: 1.06 (2H, m), 1.28 (3H, m), 1.38 (2H, m), 1.59 (1H, m), 1.88-2.40 (4H, m), 2.49 (1H, m), 3.20-3.82 (5H, m), 4.30 (2H, m), 6.98 (1H, m), 7.53 (2H, m), 7.90 (2H, m)

Step 2: Ethyl 2-((S)-3-((R)-2-(4-(cyclopropylsulfonyl)phenyl)-3-((5-fluorothiazol-2-yl)amino)-3-oxopropyl)pyrrolidin-1-yl)-2-oxoacetate (78.4 mg, 150 μmol) was dissolved in methylamine (2 M tetrahydrofuran solution, 4 mL), and the obtained mixture was then stirred for 7 hours. Thereafter, the reaction solution was concentrated in vacuo, and the obtained residue was then purified by silica gel chromatography (chloroform/methanol=2%→7%) to obtain the captioned compound (61.1 mg, 80%) in the form of a white solid.

$^1$H-NMR (CDCl$_3$) δ: 1.07 (2H, m), 1.38 (2H, m), 1.80-2.42 (4H, m), 2.50 (1H, m), 2.70 (3H, m), 3.28 (1H, m), 3.62-3.88 (3H, m), 4.18 (1H, m), 6.98 (1H, m), 7.57 (2H, m), 7.90 (2H, m)

Example 12

Production of (S)—N-((1-acetylazetidin-3-yl)methyl)-3-((R)-2-(4-(cyclopropylsulfonyl)phenyl)-3-((5-fluorothiazol-2-yl)amino)-3oxopropyl)pyrrolidine-1-carboxamide Step 1: tert-Butyl 3-(aminomethyl)azetidine-1-carboxylate (1.10 g, 5.91 mmol) was dissolved in dichloromethane (50 mL), and thereafter, 4-nitrophenyl chloroformate (1.19 g, 5.91 mmol) and pyridine (0.47 g, 5.91 mmol) were added to the obtained solution. The obtained mixture was stirred for 16 hours. Thereafter, the reaction solution was concentrated in vacuo to obtain tert-butyl 3-((((4-nitrophenoxy)carbonyl)amino)methyl)azetidine-1-carboxylate (2.52 g, quant) in the form of a white solid.

$^1$H-NMR (CDCl$_3$) δ: 1.45 (9H, s), 2.80 (1H, m), 3.52 (2H, m), 3.69 (2H, m), 4.06 (2H, m), 7.32 (2H, d, J=9.0 Hz), 8.25 (2H, d, J=9.0 Hz)

Step 2: The captioned compound was obtained in the form of a white solid by performing the same reactions and treatments as those in Step 2 of Example 2, Step 1 of Example 2, and Example 3, with the exception that tert-butyl 3-((((4-nitrophenoxy)carbonyl)amino)methyl)azetidine-1-carboxylate was used instead of phenyl N-methylcarbamate.

$^1$H-NMR (CDCl$_3$) δ: 1.06 (2H, m), 1.36 (2H, m), 1.42-1.70 (1H, m), 1.88 (3H, s), 1.82-2.23 (4H, m), 2.46 (1H, m), 2.76 (1H, m), 3.11-3.76 (6H, m), 3.85 (2H, m), 4.03 (2H, m), 4.19 (1H, m), 4.45-4.59 (1H, m), 6.97 (1H, m), 7.60 (2H, m), 7.89 (2H, m)

Example 13

Production of (R)-2-(4-(cyclopropylsulfonyl)phenyl)-N-(5-fluorothiazol-2-yl)-3-((S)-1-(2-hydroxyacetyl)pyrrolidin-3-yl)propanamide Step 1: 2-((S)-3-((R)-2-(4-(Cyclopropylsulfonyl)phenyl)-3-((5-fluorothiazol-2-yl)amino)-3-oxopropyl)pyrrolidin-1-yl)-2-oxoethyl acetate was obtained in the form of a white solid by performing the same reaction and treatment as those in Example 3, with the exception that acetoxyacetyl chloride was used instead of acetyl chloride.

$^1$H-NMR (CDCl$_3$) δ: 1.03 (2H, m), 1.42 (2H, m), 1.67 (1H, m), 1.92 (3H, s), 2.10 (3H, m), 2.32 (1H, m), 2.48 (1H, m), 3.05-4.02 (5H, m), 4.62 (2H, m), 6.95 (1H, m), 7.60 (2H, m), 7.85 (2H, m)

Step 2: 2-((S)-3-((R)-2-(4-(Cyclopropylsulfonyl)phenyl)-3-((5-fluorothiazol-2-yl)amino)-3-oxopropyl)pyrrolidin-1-yl)-

2-oxoethyl acetate (47.0 mg, 89.8 μmol) was dissolved in tetrahydrofuran (1 mL) and methanol (1 mL), and thereafter, an aqueous solution of sodium hydroxide (2 M, 0.36 mL) was added to the obtained solution under ice-cold condition. The obtained mixture was stirred for 30 minutes. Thereafter, water was added to the reaction solution, and the mixed solution was then extracted with ethyl acetate. The organic layer was dried over anhydrous sodium sulfate, and was then concentrated in vacuo. The obtained residue was purified by silica gel chromatography (chloroform/methanol=1%→15%) to obtain the captioned compound (38.2 mg, 88%) in the form of a white solid.

$^1$H-NMR (DMSO-$d_6$) δ: 0.95-1.07 (4H, m), 1.50 (1H, m), 1.72-1.95 (3H, m), 2.13 (1H, m), 2.80 (1H, m), 2.92 (1H, m), 3.15 (1H, m), 3.41 (1H, m), 3.82-3.97 (3H, m), 4.40 (1H, m), 7.26 (1H, m), 7.61 (2H, m), 7.82 (2H, m).

Example 14

Production of (S)-3-((R)-2-(4-(cyclopropylsulfonyl)phenyl)-3-((5-methoxythiazol-2-yl)amino)-3-oxopropyl)-N-methylpyrrolidine-1-carboxamide The captioned compound was obtained in the form of a white solid by performing the same reactions and treatments as those in Step 7 of Example 1 and Example 2, with the exception that 2-amino-5-methoxythiazole was used instead of 2-amino-5-fluorothiazole.

$^1$H-NMR (CDCl$_3$) δ: 1.05 (2H, m), 1.35 (2H, m), 1.52-1.68 (1H, m), 1.89-2.16 (3H, m), 2.21 (1H, m), 2.46 (1H, m), 2.80 (3H, d, J=4.6 Hz), 3.06 (1H, m), 3.18 (1H, m), 3.37 (1H, m), 3.59 (1H, m), 3.78 (1H, m), 3.88 (3H, m), 4.16 (1H, m), 6.68 (1H, s), 7.55 (2H, d, J=8.5 Hz), 7.87 (2H, d, J=8.5 Hz).

Example 15

Production of (S)-3-((R)-3-((5-chlorothiazol-2-yl)amino)-2-(4-(cyclopropylsulfonyl)phenyl)-3-oxopropyl)-N-methylpyrrolidine-1-carboxamide The captioned compound was obtained in the form of a white solid by performing the same reactions and treatments as those in Step 7 of Example 1 and Example 2, with the exception that 2-amino-5-chlorothiazole was used instead of 2-amino-5-fluorothiazole.

$^1$H-NMR (CDCl$_3$) δ: 1.05 (2H, m), 1.36 (2H, m), 1.91-2.08 (2H, m), 2.19 (2H, m), 2.46 (1H, m), 2.78 (3H, d, J=4.6 Hz), 3.12-3.22 (2H, m), 3.36 (1H, m), 3.65 (1H, m), 4.00 (1H, m), 4.28 (1H, m), 7.20 (1H, s), 7.61 (2H, d, J=8.5 Hz), 7.86 (2H, d, J=8.5 Hz)

Example 16

Production of (S)-3-((R)-2-(4-(cyclopropylsulfonyl)phenyl)-3-((5-methylthiazol-2-yl)amino)-3-oxopropyl)-N-methylpyrrolidine-1-carboxamide The captioned compound was obtained in the form of a white solid by performing the same reactions and treatments as those in Step 7 of Example 1 and Example 2, with the exception that 2-amino-5-methylthiazole was used instead of 2-amino-5-fluorothiazole.

$^1$H-NMR (CDCl$_3$) δ: 1.05 (2H, m), 1.35 (2H, m), 1.98 (2H, m), 2.09 (1H, m), 2.23 (1H, m), 2.40 (3H, s), 2.45 (1H, m), 2.79 (3H, d, J=4.9 Hz), 3.05 (1H, m), 3.17 (1H, m), 3.37 (1H, m), 3.60 (1H, m), 3.82 (1H, m), 4.20 (1H, m), 7.07 (1H, s), 7.54 (2H, d, J=8.5 Hz), 7.84 (2H, d, J=8.5 Hz)

Example 17

Production of (S)-3-((R)-2-(4-(cyclopropylsulfonyl)phenyl)-3-((5-methylpyrazin-2-yl)amino)-3-oxopropyl)-N-methylpyrrolidine-1-carboxamide The captioned compound was obtained in the form of a white solid by performing the same reactions and treatments as those in Step 7 of Example 1 and Example 2, with the exception that 5-methylpyrazin-2-amine was used instead of 2-amino-5-fluorothiazole.

$^1$H-NMR (CDCl$_3$) δ: 1.05 (2H, m), 1.36 (2H, m), 1.98 (2H, m), 2.12 (1H, m), 2.21 (1H, m), 2.48 (1H, m), 2.51 (3H, s), 2.78 (3H, d, J=4.5 Hz), 3.07 (1H, m), 3.20 (1H, m), 3.39 (1H, m), 3.62 (1H, m), 3.84 (1H, m), 4.15 (1H, m), 7.59 (2H, d, J=8.5 Hz), 7.89 (2H, d, J=8.5 Hz), 8.07 (1H, s), 9.39 (1H, s)

Example 18

Production of (S)-3-((R)-2-(4-(cyclopropylsulfonyl)phenyl)-3-((1-methyl-1H-pyrazol-3-yl)amino)-3-oxopropyl)-N-methylpyrrolidine-1-carboxamide The captioned compound was obtained in the form of a white solid by performing the same reactions and treatments as those in Step 7 of Example 1 and Example 2, with the exception that 1-methyl-1H-pyrazol-3-amine was used instead of 2-amino-5-fluorothiazole.

$^1$H-NMR (CDCl$_3$) δ: 1.02 (2H, m), 1.32 (2H, m), 1.52 (1H, m), 1.95 (3H, m), 2.13 (1H, m), 2.44 (1H, m), 2.73 (3H, d, J=5.0 Hz), 2.95 (1H, m), 3.12 (1H, m), 3.34 (1H, m), 3.52 (1H, m), 3.69 (3H, s), 4.33 (1H, m), 6.58 (1H, d, J=2.3 Hz), 7.19 (1H, d, J=2.3 Hz), 7.55 (2H, d, J=8.5 Hz), 7.78 (2H, d, J=8.5 Hz), 9.09 (1H, s).

Example 19

Production of (S)-3-((R)-2-(4-(cyclopropylsulfonyl)phenyl)-3-((5-methylpyridin-2-yl)amino)-3-oxopropyl)-N-methylpyrrolidine-1-carboxamide The captioned compound was obtained in the form of a white solid by performing the same reactions and treatments as those in Step 7 of Example 1 and Example 2, with the exception that 5-methylpyridin-2-amine was used instead of 2-amino-5-fluorothiazole.

$^1$H-NMR (DMSO-$d_6$) δ: 0.97 (2H, m), 1.06 (2H, m), 1.46 (1H, m), 1.79 (2H, m), 1.90 (1H, m), 2.10 (1H, m), 2.18 (3H, s), 2.49 (3H, d, J=4.1 Hz), 2.78 (2H, m) 3.02 (1H, m), 3.23 (1H, m), 3.37 (1H, m), 4.04 (1H, m), 5.89 (1H, d, J=4.1 Hz), 7.53 (1H, dd, J=2.3, 8.2 Hz), 7.63 (2H, d, J=8.2 Hz), 7.82 (2H, d, J=8.2 Hz), 7.91 (1H, d, J=8.2 Hz), 8.09 (1H, d, J=2.3 Hz).

Example 20

Production of 6-((R)-2-(4-(cyclopropylsulfonyl)phenyl)-3-((S)-1-(methylcarbamoyl)pyrrolidin-3-yl)propanamido)nicotinic acid Step 1: Benzyl 6-((R)-2-(4-(cyclopropylsulfonyl)phenyl)3-((S)-1-(methylcarbamoyl)pyrrolidin-3-yl)-propanamido)nicotinate was obtained in the form of a white solid by performing the same reactions and treatments as those in Step 7 of Example 1 and Example 2, with the exception that benzyl 6-aminonicotinate was used instead of 2-amino-5-fluorothiazole.

¹H-NMR (CDCl₃) δ: 1.01 (2H, m), 1.33 (2H, m), 1.60 (1H, m), 1.90-2.30 (3H, m), 2.43 (1H, m), 2.78 (3H, m), 3.02 (1H, m), 3.17 (1H, m), 3.37 (1H, m), 3.60 (1H, m), 3.96 (1H, m), 4.33 (1H, m), 5.32 (2H, s), 7.35 (5H, m), 7.60 (2H, m), 7.83 (2H, m), 8.22 (2H, m), 8.84 (1H, m)

Step 2: Benzyl 6-((R)-2-(4-(cyclopropylsulfonyl)phenyl)3-((S)-1-(methylcarbamoyl)pyrrolidin-3-yl)-propanamido) nicotinate (50.0 mg, 84.6 µmol) was dissolved in ethyl acetate (2 mL), and thereafter, 10% palladium carbon (catalytic amount) was added to the obtained solution. The obtained mixture was stirred under a hydrogen atmosphere for 15 hours. Thereafter, the reaction solution was filtered through a pad of celite, and was then concentrated in vacuo, so as to obtain the captioned compound (28.8 mg, 68%) in the form of a white solid.

¹H-NMR (DMSO-d₆) δ: 0.95-1.05 (4H, m), 1.46 (1H, m), 1.68-1.92 (3H, m), 2.10 (1H, m), 2.60 (3H, m), 2.78 (2H, m), 3.02 (1H, m), 3.20-3.45 (2H, m), 4.08 (1H, m), 5.89 (1H, m), 7.63 (2H, m), 7.82 (2H, m), 8.11 (1H, d, J=8.2 Hz), 8.17 (1H, d, J=8.2 Hz), 8.75 (1H, s).

Example 21

Production of (S)-3-((R)-2-(4-(cyclopropylsulfonyl)phenyl)-3-((5-methylpyridin-2-yl)amino)-3-oxopropyl)pyrrolidine-1-carboxamide The captioned compound was obtained in the form of a white solid by performing the same reactions and treatments as those in Step 7 of Example 1, Step 1 of Example 2, and Example 4, with the exception that 5-methylpyridin-2-amine was used instead of 2-amino-5-fluorothiazole.

¹H-NMR (DMSO-d₆) δ: 0.95-1.08 (4H, m), 1.48 (1H, m), 1.68-1.94 (3H, m), 2.11 (1H, m), 2.18 (3H, s), 2.78 (2H, m), 3.02 (1H, m), 3.24 (1H, m), 3.38 (1H, m), 4.04 (1H, m), 5.58 (2H, s), 7.53 (1H, dd, J=2.3, 8.7 Hz), 7.63 (2H, m), 7.82 (2H, m), 7.91 (1H, d, J=8.7 Hz), 8.09 (1H, d, J=2.3 Hz).

Example 22

Production of (S)-3-((R)-2-(4-(cyclopropylsulfonyl)phenyl)-3-((5-methylpyridin-2-yl)amino)-3-oxopropyl)-N-ethylpyrrolidine-1-carboxamide The captioned compound was obtained in the form of a white solid by performing the same reactions and treatments as those in Step 7 of Example 1, Step 1 of Example 2, and Example 4, with the exceptions that 5-methylpyridin-2-amine was used instead of 2-amino-5-fluorothiazole, and that ethyl isocyanate was used instead of trimethylsilyl isocyanate.

¹H-NMR (DMSO-d₆) δ: 0.90-1.05 (7H, m), 1.45 (1H, m), 1.62-1.92 (3H, m), 2.08 (1H, m), 2.19 (3H, s), 2.77 (2H, m), 2.98-3.05 (3H, m), 3.22 (1H, m), 3.40 (1H, m), 4.03 (1H, m), 5.92 (1H, m), 7.54 (1H, d, J=8.2 Hz), 7.63 (2H, m), 7.81 (2H, m), 7.90 (1H, d, J=8.2 Hz), 8.09 (1H, s).

Example 23

Production of (R)-3-((S)-1-acetylpyrrolidin-3-yl)-2-(4-(cyclopropylsulfonyl)phenyl)-N-(5-methylpyridin-2-yl)propanamide The captioned compound was obtained in the form of a white solid by performing the same reactions and treatments as those in Step 7 of Example 1, Step 1 of Example 2, and Example 3, with the exception that 5-methylpyridin-2-amine was used instead of 2-amino-5-fluorothiazole.

¹H-NMR (DMSO-d₆) δ: 0.96 (2H, m), 1.06 (2H, m), 1.55 (1H, m), 1.65-2.10 (7H, m), 2.20 (3H, s), 2.79 (2H, m), 3.04 (1H, m), 3.32 (1H, m), 3.50 (1H, m), 4.06 (1H, m), 7.55 (1H, d, J=8.2 Hz), 7.63 (2H, m), 7.82 (2H, m), 7.91 (1H, d, J=8.2 Hz), 8.10 (1H, s).

Example 24

Production of 6-((R)-3-((S)-1-acetylpyrrolidin-3-yl)-2-(4-(cyclopropylsulfonyl)phenyl)propanamido) nicotinic acid The captioned compound was obtained in the form of a white solid by performing the same reactions and treatments as those in Step 7 of Example 1, Step 1 of Example 2, Example 3, and Step 2 of Example 20, with the exception that benzyl 6-aminonicotinate was used instead of 2-amino-5-fluorothiazole.

¹H-NMR (DMSO-d₆) δ: 1.03 (2H, m), 1.08 (2H, m), 1.52 (1H, m), 1.80-2.05 (6H, m), 2.20 (1H, m), 2.83 (2H, m), 3.08 (1H, m), 3.35-3.60 (2H, m), 4.16 (1H, m), 7.68 (2H, m), 7.86 (2H, m), 8.16 (1H, d, J=8.2 Hz), 8.22 (1H, d, J=8.2 Hz), 8.80 (1H, s).

Example 25

Production of 6-((R)-2-(4-(cyclopropylsulfonyl)phenyl)-3-((S)-1-(ethylcarbamoyl)pyrrolidin-3-yl)propanamido)nicotinic acid The captioned compound was obtained in the form of a white solid by performing the same reactions and treatments as those in Step 7 of Example 1, Step 1 of Example 2, Example 4, and Step 2 of Example 20, with the exceptions that benzyl 6-aminonicotinate was used instead of 2-amino-5-fluorothiazole, and that ethyl isocyanate was used instead of trimethylsilyl isocyanate.

¹H-NMR (DMSO-d₆) δ: 0.92-1.05 (7H, m), 1.46 (1H, m), 1.70-1.95 (3H, m), 2.12 (1H, m), 2.75 (2H, m), 2.94-3.05 (3H, m), 3.25-3.39 (2H, m), 4.09 (1H, m), 5.93 (1H, m), 7.64 (2H, m), 7.82 (2H, m), 8.11 (1H, d, J=8.2 Hz), 8.16 (1H, d, J=8.2 Hz), 8.75 (1H, s).

Example 26

Production of (R)-3-((S)-1-acetylpyrrolidin-3-yl)-2-(4-(cyclopropylsulfonyl)phenyl)-N-(5-methoxythiazol-2-yl)propanamide The captioned compound was obtained in the form of a white solid by performing the same reactions and treatments as those in Step 7 of Example 1, Step 1 of Example 2, and Example 3, with the exception that 2-amino-5-methoxythiazole was used instead of 2-amino-5-fluorothiazole.

¹H-NMR (DMSO-d₆) δ: 1.03 (2H, m), 1.12 (2H, m), 1.52 (1H, m), 1.77-1.98 (6H, m), 2.13 (1H, m), 2.83 (2H, m), 3.06 (1H, m), 3.40-3.52 (2H, m), 3.82 (3H, s), 3.95 (1H, m), 6.83 (1H, s), 7.65 (2H, d, J=8.5 Hz), 7.88 (2H, d, J=8.5 Hz)

Example 27

Production of 2-((R)-3-((S)-1-acetylpyrrolidin-3-yl)-2-(4-(cyclopropylsulfonyl)phenyl)propanamido)thiazole-5-carboxylic acid The captioned compound was obtained in the form of a white solid by performing the same reactions and treatments as those in Step 7 of Example 1, Step 1 of Example 2, Example 3, and Step 2 of Example 13, with the exception that ethyl 2-aminothiazole-5-carboxylate was used instead of 2-amino-5-fluorothiazole.

$^1$H-NMR (DMSO-$d_6$) δ: 0.95-1.07 (4H, m), 1.30-1.55 (1H, m), 1.72-1.98 (6H, m), 2.13 (1H, m), 2.79 (2H, m), 3.01 (1H, m), 3.30-3.58 (2H, m), 4.03 (1H, m), 7.62 (2H, m), 7.84 (2H, m), 8.00 (1H, s).

The chemical structures of some compounds included in the present invention are shown in Table 1-1 and Table 1-2 below.

TABLE 1-1

| Example | Structural formula |
|---|---|
| 1 | |
| 2 | |
| 3 | |
| 4 | |
| 5 | |
| 6 | |
| 7 | |
| 8 | |

TABLE 1-1-continued
| Example | Structural formula |
|---|---|
| 9 | 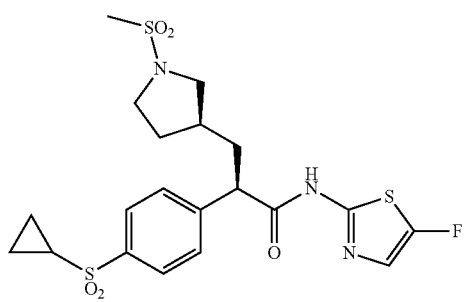 [SMILES: CS(=O)(=O)N1CC[C@H](C[C@@H](C(=O)Nc2ncc(F)s2)c2ccc(S(=O)(=O)C3CC3)cc2)C1] |
| 10 | 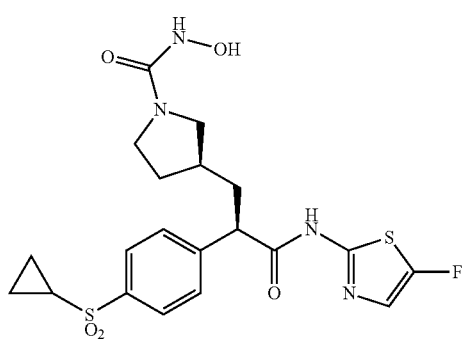 [SMILES: O=C(Nc1ncc(F)s1)[C@H](C[C@H]1CCN(C(=O)NO)C1)c1ccc(S(=O)(=O)C2CC2)cc1] |
| 11 | 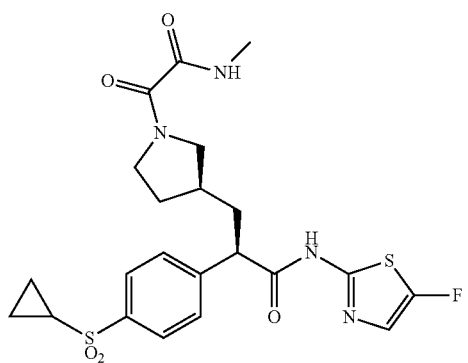 [SMILES: CNC(=O)C(=O)N1CC[C@H](C[C@@H](C(=O)Nc2ncc(F)s2)c2ccc(S(=O)(=O)C3CC3)cc2)C1] |
| 12 | 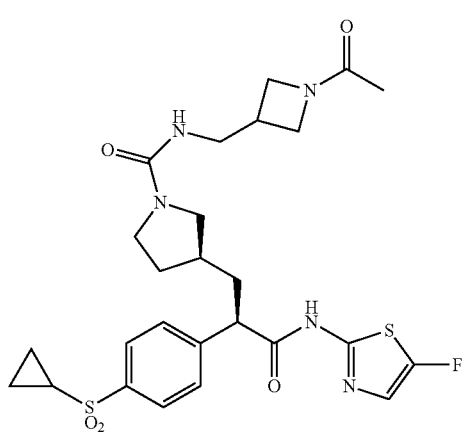 [SMILES: CC(=O)N1CC(CNC(=O)N2CC[C@H](C[C@@H](C(=O)Nc3ncc(F)s3)c3ccc(S(=O)(=O)C4CC4)cc3)C2)C1] |
TABLE 1-1-continued
| Example | Structural formula |
|---|---|
| 13 | 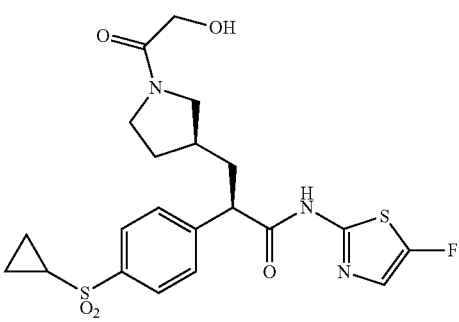 [SMILES: O=C(Nc1ncc(F)s1)[C@H](C[C@H]1CCN(C(=O)CO)C1)c1ccc(S(=O)(=O)C2CC2)cc1] |
| 14 | |
TABLE 1-2
| Example | Structural formula |
|---|---|
| 15 | |
| 16 | |

TABLE 1-2-continued
| Example | Structural formula |
|---|---|
| 17 | 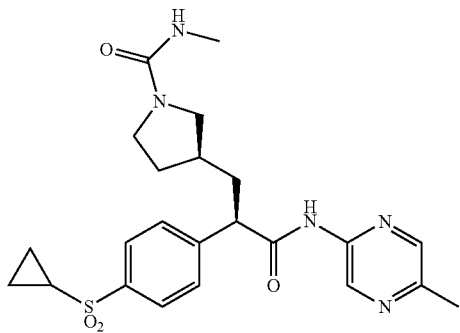 [SMILES: CNC(=O)N1CC[C@H](C[C@@H](C(=O)Nc2cnc(C)cn2)c2ccc(S(=O)(=O)C3CC3)cc2)C1] |
| 18 | 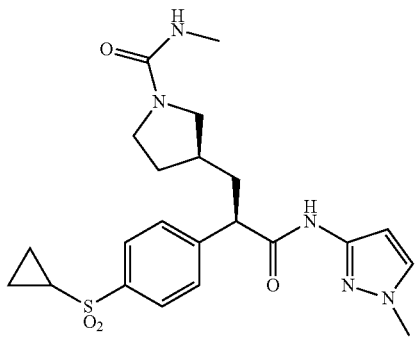 [SMILES: CNC(=O)N1CC[C@H](C[C@@H](C(=O)Nc2ccn(C)n2)c2ccc(S(=O)(=O)C3CC3)cc2)C1] |
| 19 | 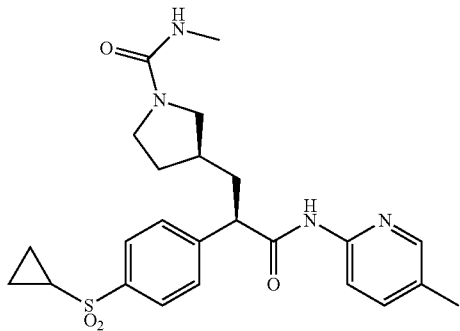 [SMILES: CNC(=O)N1CC[C@H](C[C@@H](C(=O)Nc2ccc(C)cn2)c2ccc(S(=O)(=O)C3CC3)cc2)C1] |
| 20 | 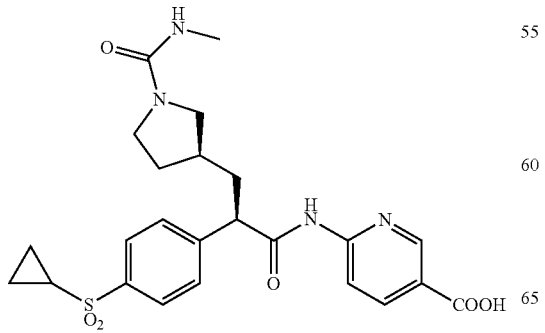 |
| 21 | 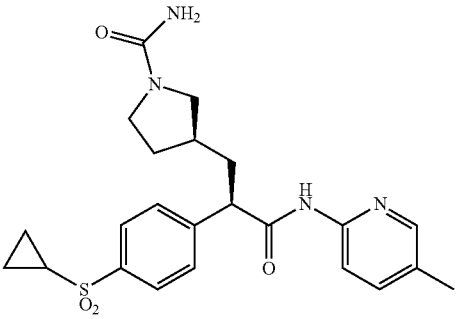 [SMILES: Cc1ccc(NC(=O)[C@H](C[C@H]2CCN(C(N)=O)C2)c2ccc(S(=O)(=O)C3CC3)cc2)nc1] |
| 22 | 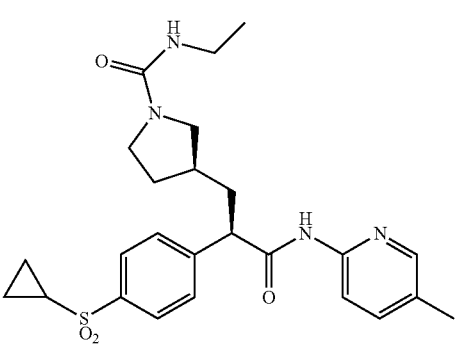 [SMILES: CCNC(=O)N1CC[C@H](C[C@@H](C(=O)Nc2ccc(C)cn2)c2ccc(S(=O)(=O)C3CC3)cc2)C1] |
| 23 | 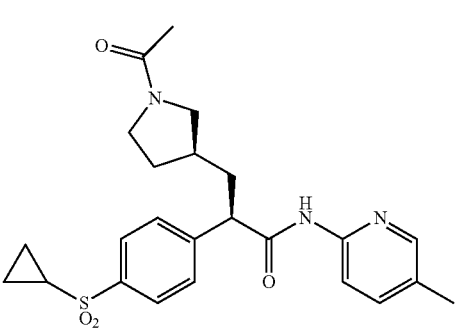 [SMILES: CC(=O)N1CC[C@H](C[C@@H](C(=O)Nc2ccc(C)cn2)c2ccc(S(=O)(=O)C3CC3)cc2)C1] |
| 24 | 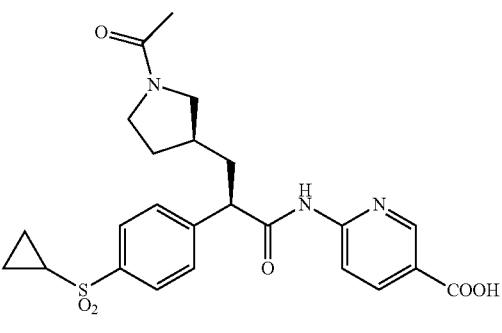 [SMILES: CC(=O)N1CC[C@H](C[C@@H](C(=O)Nc2ccc(C(=O)O)cn2)c2ccc(S(=O)(=O)C3CC3)cc2)C1] |

TABLE 1-2-continued

| Example | Structural formula |
|---|---|
| 25 | |
| 26 | |
| 27 | |

Test Example 1

In Vitro GK Activating Action (1) Preparation of GK Fusion Protein cDNA (GenBank Accession No. NM_033507, human glucokinase, variant 2) encoding human liver-type GK polypeptide was cloned by performing a polymerase chain reaction (hereinafter referred to as "PCR") using a human liver cDNA library (Human liver QUICK-Clone cDNA, TAKARA BIO INC.), and the thus cloned cDNA was then introduced into an expression vector (pGEX-3X, GE Healthcare Japan) for glutathione S transferase (hereinafter referred to as GST) fusion proteins. The resulting vector was introduced into *Escherichia coli* (Competent high DH5α, Toyobo Co., Ltd.), and the transformed *Escherichia coli* was then cultured at 37° C. Thereafter, Isopropyl β-D-1-thiogalactopyranoside (final concentration: 1 mmol/L, Sigma Aldrich Japan) was added to the culture, and the obtained mixture was then cultured at 30° C. for 3 hours. Thereafter, a cell mass was recovered. The recovered cell mass was subjected to freezing-and-thawing, and the resulting cell mass was then suspended in Triton-X that had been added in a final concentration of 1% to a phosphate buffer, followed by disintegration with an ultrasonic disintegrator. The homogenate was centrifuged at 33,200 rpm at 4° C. for 1 hour. Thereafter, the supernatant was recovered, and a GST-GK fusion protein was then purified using a glutathione column (GSTrap FF, GE Healthcare Japan). The obtained GST-GK fusion protein was divided into some portions each having a small volume, and the thus divided proteins were then preserved at −80° C.

(2) In Vitro GK Activating Action Measurement Test

A GK assay was carried out at 25° C. at a final incubation volume of 100 µL using a flat-bottom 96-well assay plate. An assay buffer comprised 25 mmol/L Hepes buffer (pH 7.1), 25 mmol/L KCl, 2.5 mmol/L or 10 mmol/L D-glucose, 5 mmol/L ATP, 1 mmol/L nicotinamide adenine dinucleotide phosphate (abbreviated as NADP), 2 mmol/L $MgCl_2$, 1 mmol/L dithiothreitol (DTT), 2 units/mL glucose-6 phosphate dehydrogenase (G6PDH), and 1 µg/mL GST-GK derived from human liver GK. ATP, G6PDH, and NADP were purchased from Roche Diagnostics. Other reagents were purchased from Wako Pure Chemical Industries, Ltd. 10 µL of the test compound solution dissolved in dimethyl sulfoxide (DMSO) was added to the flat-bottom 96-well assay plate, and thereafter, 80 µL of assay buffer that did not contain GST-GK was added thereto. The thus mixed solution was preincubated in an incubator in which the temperature was controlled at 25° C. for 15 minutes. Subsequently, the reaction was initiated by adding 10 µL of the GST-GK solution to the reaction mixture, resulting in a final concentration of 0.1 µg/mL. After initiation of the reaction, an increase in the optical concentration at 340 nm (OD340) was monitored with a microplate spectrophotometer (Varsamax, Molecular Devices Japan K. K.) every 10 seconds over an incubation period of 10 minutes. An inclination of the OD340 increase was defined as raw data. The GK activating rate was indicated as a numerical value obtained from the expression: (Inclination of OD340 increase by addition of the test compound)/(inclination of OD340 increase without addition of the test compound). The results of the GK activating rate obtained at a test compound concentration of 1 µmol/L under the condition of a glucose concentration of 2.5 mmol/L are shown in the following table 2.

TABLE 2

| Example No. | GK activation rate (%) |
|---|---|
| 2 | 1018 |
| 3 | 803 |
| 4 | 1287 |
| 5 | 561 |
| 6 | 422 |
| 7 | 828 |
| 8 | 535 |
| 10 | 602 |
| 11 | 427 |
| 13 | 443 |
| 14 | 809 |
| 15 | 737 |
| 16 | 484 |
| 19 | 437 |
| 21 | 727 |
| 23 | 491 |
| 26 | 877 |

As given above, it was confirmed that the compound of the present invention has a strong glucokinase-activating action.

Test Example 2

Evaluation of Organ Selectivity

A test compound suspended in 10% (v/v) Gelucire 44/14 (GATTEFOSSE) was orally administered to normal mice (C57BL/6j mice, CLEA Japan, Inc.). The percentages of drugs that had not bound to proteins in the liver and the pancreas, which had been obtained by the in vitro test, were added to the total concentrations of the drugs in the liver and the pancreas obtained 150 minutes after administration of the drugs, so as to calculate the non-binding concentration of the drug in each case. The ratio of the non-binding concentration of the drug in the pancreas to the non-binding concentration of the drug in the liver was calculated, and thus, liver selectivity was evaluated. As a comparative compound, PSN-GK1 described in non-patent document 11 (corresponding to Example 94 of patent document 2) was produced according to the method described in patent document 2, and the produced comparative compound was then evaluated in the same manner as described above (in the table, the comparative compound is indicated as PSN-GK1).

The results are shown in Table 3. As is clear from the table, it was confirmed that the compound of the present invention has higher selectivity to the liver than that of PSN-GK1.

TABLE 3

| Example No. | Dose (mg/kg) | Non-binding concentration (ng/mL) | | Selectivity |
| | | Liver | Pancreas | Liver/pancreas |
| --- | --- | --- | --- | --- |
| 2 | 30 | 23 | 0.56 | 41 |
| 3 | 10 | 65 | 3.8 | 17 |
| 5 | 30 | 47 | 1.8 | 27 |
| 19 | 10 | 10 | 0.58 | 17 |
| 21 | 10 | 50 | 2.0 | 25 |
| 23 | 3 | 3.0 | 0.33 | 9 |
| PSN-GK1 | 1 | 0.56 | 0.58 | 1.0 |
| | 3 | 1.4 | 1.7 | 0.8 |
| | 10 | 7.4 | 6.0 | 1.2 |

Test Example 3

Oral Glucose Tolerance Test with Normal Mice after Single Administration of Test Compound The test compound (Example 5) (30 mg/kg) suspended in 10%(v/v) Gelucire44/14 (GATTEFOSSE) was orally administered to normal mice (C57BL/6j mice, CLEA Japan, Inc.). Thirty minutes later, 2 g/kg glucose was orally administered to the mice. The blood glucose level was measured using an automatic blood glucose level measurement apparatus (Medisafe, TERUMO), before administration of the test compound, 25 minutes after administration of the test compound, and 15, 30, 60, and 120 minutes after administration of glucose. Thus, the action of the test compound to lower blood glucose level was evaluated.

The results are shown in FIG. 1. As is clear from the figure, the blood glucose level of the mice orally administered with the test compound was lower than that of the mice orally administered with the solvent alone. That is to say, it was confirmed that the compound of the present invention has a strong hypoglycemic action in a hyperglycemic state.

Test Example 4

Transition in Blood Glucose Levels After Completion of Single Administration of Test Compound to Normal Mice A test compound (30 mg/kg, Example 5) suspended in 10% (v/v) Gelucire 44/14 (GATTEFOSSE) was orally administered to normal mice (C57BL/6j mice, CLEA Japan, Inc.). The blood glucose level was measured using an automatic blood glucose level measurement apparatus (Medisafe, TERUMO), before administration of the test compound, and 1, 2, 4, and 6 hours after administration of the test compound. Thus, the hypoglycemic action of the test compound was evaluated.

Figure 2:
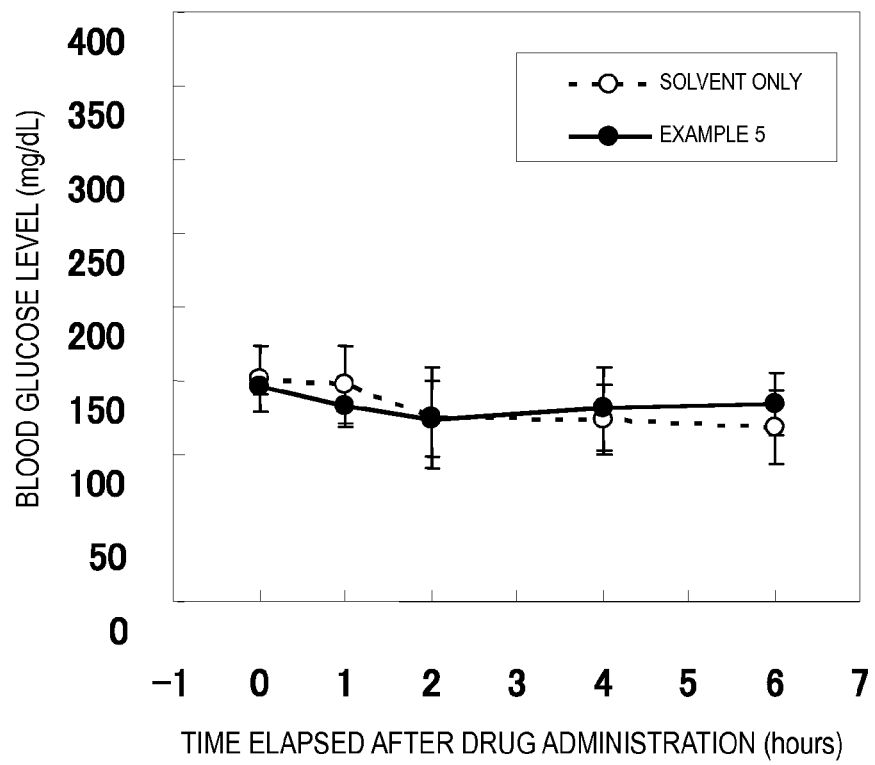
FIG. 2 is a view showing a transition in the blood glucose levels after completion of a single administration of the compound of the present invention to normal mice.

The results are shown in FIG. 2. As is clear from the figure, the blood glucose level of the mice orally administered with the test compound was almost equal to the blood glucose level of the mice orally administered with the solvent alone. That is, it was confirmed that the compound of the present invention does not show a hypoglycemic action in an ordinary blood glucose state, and thus that it has a low hypoglycemia risk.

INDUSTRIAL APPLICABILITY

Since the phenylacetamide compound represented by the formula (1) of the present invention, or a salt thereof, or a solvate of the compound or the salt has an excellent glucokinase-activating action and is useful for preventing and/or treating diabetes, it is industrially applicable.

The invention claimed is:
1. A compound represented by the following formula (1), or a salt thereof, or a solvate of the compound or the salt:

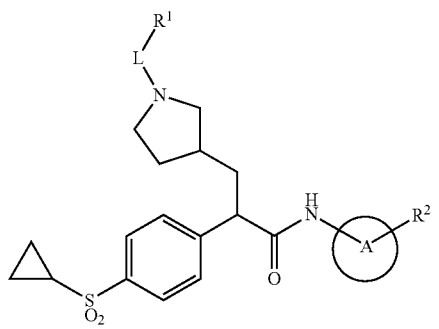

(1)

wherein ring A represents a thiazolyl group, a pyridyl group, a pyrazyl group, or a pyrazolyl group, L represents —(CO)—, —(CS)—, or —(SO$_2$)—, R$^1$ represents a C$_{1-6}$ alkyl group, a hydroxy C$_{1-6}$ alkyl group, a C$_{1-6}$ alkoxy group, an amino group, a C$_{1-6}$ alkylamino group, a hydroxyamino group, an N—C$_{1-6}$ alkylcarbamoyl group, or a group represented by the following formula (2):

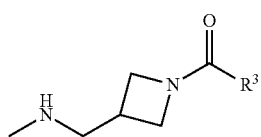

(2)

wherein R$^3$ represents a C$_{1-6}$ alkyl group, and

R$^2$ represents a hydrogen atom, a halogen atom, a C$_{1-6}$ alkyl group, a C$_{1-6}$ alkoxy group, or a carboxyl group.

2. The compound or a salt thereof, or a solvate of the compound or the salt according to claim 1, wherein the compound represented by the formula (1) is (S)-tert-butyl 3-((R)-2-(4-(cyclopropylsulfonyl)phenyl)-3-((5-fluorothiazol-2-yl)amino)-3-oxopropyl)pyrrolidine-1-carboxylate,
(S)-3-((R)-2-(4-(cyclopropylsulfonyl)phenyl)-3-((5-fluorothiazol-2-yl)amino)-3-oxopropyl)-N-methylpyrrolidine-1-carboxamide,
(R)-3-((S)-1-acetylpyrrolidin-3-yl)-2-(4-(cyclopropylsulfonyl)phenyl)-N-(5-fluorothiazol-2-yl)propanamide,
(S)-3-((R)-2-(4-(cyclopropylsulfonyl)phenyl)-3-((5-fluorothiazol-2-yl)amino)-3-oxopropyl)pyrrolidine-1-carboxamide,
(S)-3-((R)-2-(4-(cyclopropylsulfonyl)phenyl)-3-((5-fluorothiazol-2-yl)amino)-3-oxopropyl)-N-ethylpyrrolidine-1-carboxamide,
(S)-3-((R)-2-(4-(cyclopropylsulfonyl)phenyl)-3-((5-fluorothiazol-2-yl)amino)-3-oxopropyl)-N-propylpyrrolidine-1-carboxamide,
(S)-methyl 3-((R)-2-(4-(cyclopropylsulfonyl)phenyl)-3-((5-fluorothiazol-2-yl)amino)-3-oxopropyl)pyrrolidine-1-carboxylate,
(R)-2-(4-(cyclopropylsulfonyl)phenyl)-N-(5-fluorothiazol-2-yl)-3-((S)-1-(methylcarbamothioyl)pyrrolidin-3-yl)propanamide,
(R)-2-(4-(cyclopropylsulfonyl)phenyl)-N-(5-fluorothiazol-2-yl)-3-((S)-1-(methylsulfonyl)pyrrolidin-3-yl)propanamide,
(S)-3-((R)-2-(4-(cyclopropylsulfonyl)phenyl)-3-((5-fluorothiazol-2-yl)amino)-3-oxopropyl)-N-hydroxypyrrolidine-1-carboxamide,
(R)-2-(4-(cyclopropylsulfonyl)phenyl)-N-(5-fluorothiazol-2-yl)-3-((S)-1-(methylamino)-2-oxoacetyl)pyrrolidin-3-yl)propanamide,
(S)—N-((1-acetylazetidin-3-yl)methyl)-3-4R)-2-(4-(cyclopropylsulfonyl)phenyl)-3-((5-fluorothiazol-2-yl)amino)-3-oxopropyl)pyrrolidine-1-carboxamide,
(R)-2-(4-(cyclopropylsulfonyl)phenyl)-N-(5-fluorothiazol-2-yl)-3-((S)-1-(2-hydroxyacetyl)pyrrolidin-3-yl)propanamide,
(S)-3-((R)-2-(4-(cyclopropylsulfonyl)phenyl)-3-((5-methoxythiazol-2-yl)amino)-3-oxopropyl)-N-methylpyrrolidine-1-carboxamide,
(S)-3-((R)-3-((5-chlorothiazol-2-yl)amino)-2-(4-(cyclopropylsulfonyl)phenyl)-3-oxopropyl)-N-methylpyrrolidine-1-carboxamide,
(S)-3-((R)-2-(4-(cyclopropylsulfonyl)phenyl)-3-((5-methylthiazol-2-yl)amino)-3-oxopropyl)-N-methylpyrrolidine-1-carboxamide,
(S)-3-((R)-2-(4-(cyclopropylsulfonyl)phenyl)-3-((5-methylpyrazin-2-yl)amino)-3-oxopropyl)-N-methylpyrrolidine-1-carboxamide,
(S)-3-((R)-2-(4-(cyclopropylsulfonyl)phenyl)-3-((1-methyl-1H-pyrazol-3-yl)amino)-3-oxopropyl)-N-methylpyrrolidine-1-carboxamide,
(S)-3-((R)-2-(4-(cyclopropylsulfonyl)phenyl)-3-((5-methylpyridin-2-yl)amino)-3-oxopropyl)-N-methylpyrrolidine-1-carboxamide,
6-((R)-2-(4-(cyclopropylsulfonyl)phenyl)-3-((S)-1-(methylcarbamoyl)pyrrolidin-3-yl)propanamido)nicotinic acid,
(S)-3-((R)-2-(4-(cyclopropylsulfonyl)phenyl)-3-((5-methylpyridin-2-yl)amino)-3-oxopropyl)pyrrolidine-1-carboxamide,
(S)-3-((R)-2-(4-(cyclopropylsulfonyl)phenyl)-3-((5-methylpyridin-2-yl)amino)-3-oxopropyl)-N-ethylpyrrolidine-1-carboxamide,
(R)-3-((S)-1-acetylpyrrolidin-3-yl)-2-(4-(cyclopropylsulfonyl)phenyl)-N-(5-methylpyridin-2-yl)propanamide,
6-((R)-3-((S)-1-acetylpyrrolidin-3-yl)-2-(4-(cyclopropylsulfonyl)phenyl)propanamido)nicotinic acid,
6-((R)-2-(4-(cyclopropylsulfonyl)phenyl)-3-((S)-1-(ethylcarbamoyl)pyrrolidin-3-yl)propanamido)nicotinic acid,
(R)-3-((S)-1-acetylpyrrolidin-3-yl)-2-(4-(cyclopropylsulfonyl)phenyl)-N-(5-methoxythiazol-2-yl)propanamide, or
2-((R)-3-((S)-1-acetylpyrrolidin-3-yl)-2-(4-(cyclopropylsulfonyl)phenyl)propanamido)thiazole-5-carboxylic acid.

3. A pharmaceutical composition comprising the compound, or a salt thereof, or a solvate of the compound or the salt according to claim 1, and a pharmaceutically acceptable carrier.

4. A pharmaceutical composition comprising the compound, or a salt thereof, or a solvate of the compound or the salt according to claim 2, and a pharmaceutically acceptable carrier.

5. A method for activating glucokinase, the method comprising administering an effective amount of the compound or a salt thereof, or a solvate of the compound or the salt according to claim 1.

6. A method for lowering blood glucose level, the method comprising administering an effective amount of the compound or a salt thereof, or a solvate of the compound or the salt according to claim 1.

7. A method for treating at least one disease selected from the group consisting of diabetes, impaired glucose tolerance, gestational diabetes, a chronic complication of diabetes, and metabolic syndrome, wherein the method comprises administering an effective amount of the compound or a salt thereof, or a solvate of the compound or the salt according to claim 1.

8. A method for activating glucokinase, the method comprising administering an effective amount of the compound or a salt thereof, or a solvate of the compound or the salt according to claim 2.

9. A method for lowering blood glucose level, the method comprising administering an effective amount of the compound or a salt thereof, or a solvate of the compound or the salt according to claim 2.

10. A method for treating at least one disease selected from the group consisting of diabetes, impaired glucose tolerance, gestational diabetes, a chronic complication of diabetes, and metabolic syndrome, wherein the method comprises administering an effective amount of the compound or a salt thereof, or a solvate of the compound or the salt according to claim 2.

11. The method according to claim 7 wherein the chronic complication of diabetes is diabetic peripheral neuropathy, diabetic nephropathy, diabetic retinopathy, and diabetic arteriosclerosis.

12. The method according to claim 10 wherein the chronic complication of diabetes is diabetic peripheral neuropathy, diabetic nephropathy, diabetic retinopathy, and diabetic arteriosclerosis.

* * * * *